United States Patent [19]

Potter et al.

[11] Patent Number: 5,733,790
[45] Date of Patent: Mar. 31, 1998

[54] CRF BINDING PROTEIN ANTIBODIES AND ASSAYS USING SAME

[75] Inventors: Ellen Potter, La Jolla; Dominic P. Behan, San Diego, both of Calif.; Elizabeth A. Linton, Dorchester-on-Thames; Philip J. Lowry, Reading, both of England; Wylie W. Vale, Jr., La Jolla, Calif.

[73] Assignees: The Salk Institute for Biological Studies, La Jolla, Calif.; The University of Reading, Reading, United Kingdom

[21] Appl. No.: 480,756

[22] Filed: Jun. 7, 1995

Related U.S. Application Data

[63] Continuation-in-part of Ser. No. 97,828, Jul. 23, 1993, Pat. No. 5,464,757, which is a continuation-in-part of Ser. No. 967,683, Oct. 26, 1992, abandoned, which is a continuation-in-part of Ser. No. 641,341, Nov. 15, 1991, abandoned.

[51] Int. Cl.⁶ .................................................. G01N 33/543
[52] U.S. Cl. .......................... 436/518; 435/7.8; 435/7.92; 435/7.93; 435/7.94; 436/501; 436/540; 436/548; 436/811; 436/817; 530/387.1; 530/388.1; 530/388.24; 530/389.1; 530/389.2; 530/391.1; 530/391.3
[58] Field of Search ..................................... 435/7.8, 7.92, 435/7.93, 7.94; 436/501, 518, 540, 548, 811, 817; 530/387.1, 388.1, 388.24, 389.1, 389.2, 391.1, 391.3

[56] References Cited

PUBLICATIONS

Linton et al., "Carticotripin–Releasing Hormone (CRH)–Binding Protein: Reduction in the Adrenocorticotripin–Releasing Activity of Placental but no Hypothalamic CRH," *Journal of Clinical Endocrinology and Metabolism*, vol. 70, No. 6, pp. 1574–1580, (1990).

Linton et al., "Purified CRF Binding Protein Reduces at ACTH–Releasing Activity of CRF," *Journal of Endocrinology*, vol. 121, supplement, abstract 194, (Apr. 1989).

Potter et al., "The central distribution of a corticotropin–releasing factor (CRF)–binding protein predicts multiple sites and modes of interaction with CRF", *Proceedings of the National Academy of Sciences*, vol. 89, pp. 4192–4196, (1992).

Linton et al., "Comparison of a specific two–site immunoradiometric assay with radioimmunoassay for rat/human CRF–41," *Regulatory Peptides*, vol. 14, No. 1, pp. 69–84, (1986).

Linton et al., "Corticotropin Releasing Hormone–Binding Protein (CRH–BP): Plasma Levels Decrease During the Third Trimester of Normal Human Pregnancy," *Journal of Clinical Endocrinology and Metabolism*, vol. 76, No. 1, pp. 260–262, (1993).

*Primary Examiner*—Susan Wolski
*Attorney, Agent, or Firm*—Fitch, Even, Tabin & Flannery

[57] ABSTRACT

Corticotropin Releasing Factor-binding protein (CRF-BP) is produced recombinantly and is useful for modulating the biological activity of CRF. CRF-BP or fragments thereof and/or antibodies to such polypeptides are employed in diagnostic assays to determine the levels of CRF and CRF-BP and the ratio of CRF/CRF-BP in a vascular fluid sample. Following such an assay, pregnancy-related pathological disorders, such as increased risk of premature labor, can be treated, for example, by administering CRF-BP to lower the ratio of CRF/CRF-BP to within a normal range for pregnancy. Anti-CRF-BP antibodies are also useful to purify CRF-BP and to modulate the biological effect of CRF-BPs.

18 Claims, No Drawings

CRF BINDING PROTEIN ANTIBODIES AND ASSAYS USING SAME

This application is a continuation-in-part of U.S. patent application Ser. No. 08/097,828, filed Jul. 23, 1993, now U.S. Pat. No. 5,464,757 which is a continuation-in-part of U.S. patent application Ser. No. 07/967,683, filed Oct. 26, 1992 now abandoned, which is a continuation-in-part of U.S. patent application Ser. No. 07/641,341 filed Jan. 15, 1991, now abandoned.

This invention was made with Government support under Grants DK-26741 and HD-13527 awarded by the National Institutes of Health. The Government has certain rights in the invention. The University of Reading and the Medical Research Council of Great Britain also contributed financially to this invention.

This invention relates generally to controlling the biological effect of CRF in mammals and more particularly to antibodies to binding proteins for CRF which can employed therapeutically or in diagnostic assays and to such assays and the use thereof.

BACKGROUND OF THE INVENTION

Corticotropin Releasing Factor, CRF, is a very potent stimulator of the synthesis and secretion of various peptides in the human body. CRF is a 41-residue peptide which constitutes rat/human CRF (r/h CRF), the rat and human species having the same CRF molecule, the structure of which is set forth in U.S. Pat. No. 4,489,163.

Although CRF levels in human peripheral circulation are normally low, there are often elevated levels of CRF in the maternal circulation, which levels progressively increase throughout pregnancy. It has been found that the increasing concentrations of CRF in pathological cases of pregnancy, such as pregnancy-induced hypertension and pre-term labor, were substantially and significantly elevated above those found in normal pregnancies (Campbell et al., *J. Clin. Endocr. & Metab.*, 64:1054–1059, 1987).

It is believed that this maternal plasma CRF most likely originates from the placenta wherein it plays a paracrine role. Placenta cells have been shown to respond to CRF and to produce CRF and its mRNA. Even though CRF concentrations measured in late gestational maternal plasma are similar to levels reported in rat hypothalamic portal blood, which levels are capable of stimulating ACTH release in vitro, it does not appear that there is normally overproduction of ACTH during pregnancy. However, maternal plasma ACTH concentrations do increase slightly with advancing gestation.

There were reports of a protein (hereinafter termed CRF-BP) in human plasma which was capable of biologically inactivating CRF, such as Linton, E. A., et al. *Clin. Endo.* 28, 315–324 (1988) and Behan, D. P., et al. *J. Endo.* 122, 23–31 (1989) in the latter of which a partial purification process is disclosed wherein the purity of the isolated protein is estimated to be substantially higher than was later determined. It has been proposed that the role of this protein substance is the prevention of inappropriate pituitary-adrenal stimulation during pregnancy.

This CRF-BP protein is present in such minute amounts in human plasma that it is impractical to commercially extract it; moreover, purification from human plasma to such an extent that the protein could even be used clinically has heretofore not been possible. In addition, the ever-present danger of contamination by a virus, such as HIV, would have rendered any such extracted and purified protein clearly medically unacceptable in the late 1980s and thereafter. Therefore, it was certain that CRF-BP would not be practically available for clinical use unless recombinant DNA production of CRF-BP could be established, which would of course entail knowing the entire amino acid structure of the protein.

SUMMARY OF THE INVENTION

A CRF-binding protein was ultimately purified to homogeneity in an extremely minute amount and then partially characterized by amino acid (AA) sequence analysis. Oligonucleotide probes constructed on the basis of such AA sequences facilitated the cloning of cDNA encoding this CRF-BP from human liver and from rat brain libraries, and recombinant DNA molecules having nucleic acid sequences encoding CRF-BP are now provided. The recombinant rat and human CRF-BPs have been transiently transfected and expressed in COS cells which are available from the ATCC and found to bind to the 41-residue peptide which constitutes r/h CRF with high affinity. The human CRF-BP has now been stably transfected into Chinese hamster ovary (CHO) cells wherein routine expression is now occurring; as a result, recombinant CRF-BPs are now provided which are capable of binding to and modulating the biological effect of CRF and which have therapeutic applications.

CRF-BP can inhibit CRF-induced ACTH release in vitro by pituitary cells and can also inhibit CRF binding to CRF antibodies. Thus, these CRF-BPs can be administered therapeutically to bind to and inactivate CRF thereby reducing high ACTH levels in mammals caused by excess CRF and can be used to treat Cushing's Disease, and the like. These CRF-BPs are also useful in combating pituitary tumors that produce CRF. Moreover, they can be used to reduce pituitary ACTH secretion and hence reduce cortisol levels under any condition in which they are abnormally high, such as during chronic stress or in patients afflicted with anorexia nervosa or alcoholism. It has been found that CRF-BPs when administered intravenously (IV) have also proved effective to prevent CRF-induced ACTH release. Furthermore, it is considered that IV administration of the CRF-BPs can be used to raise blood pressure and in this manner combat hypotension. Fragments of CRF-BPs which bind to CRF will also modulate the bioactivity of CRF, and such fragments may be versions of the mature protein shortened at the N-terminus and/or the C-terminus. The recombinant production of such CRF-BPs and fragments thereof makes feasible their use in the foregoing manners.

Anti-CRF-BP antibodies are provided which can be made using the entire recombinant protein or a specific fragment, and some that are directed to specific epitopes of CRF-BP have been found particularly useful in diagnostic assays to determine the level of the CRF-BPs in a vascular fluid sample. Methods and diagnostic systems for determining the levels of CRF-BP and CRF, and the ratio of CRF/CRF-BP, in a vascular fluid sample using these antibodies and other antibodies are also provided. These diagnostic methods can be used for monitoring the level of therapeutically administered CRF-BP or a fragment thereof to facilitate the maintenance of an effective amount. These diagnostic methods can also be used to diagnose physiological disorders that result from higher levels of CRF or higher ratios of CRF/CRF-BP than normal. These anti-CRF-BP antibodies can also be used to purify the CRF-BP protein. Moreover, these antibodies are considered therapeutically useful to counteract the biological effect of CRF-BPs in vivo.

DETAILED DESCRIPTION OF THE PREFERRED EMBODIMENTS

Unless defined otherwise, all technical and scientific terms used herein have the same meaning as is commonly understood by one of skill in the art to which this invention belongs. All U.S. patents and all publications mentioned herein are incorporated in their entirety by reference thereto.

The amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

Amino Acid Residue: The amino acid residues described herein should be understood to be in the "L" isomeric form unless otherwise specified. If a residue in the "D" isomeric form is used, it is so identified in the polypeptide. For standard polypeptide nomenclature, see *J. Biol. Chem.*, 243:3552-3559 (1969). All amino acid residue sequences are represented herein by formulae whose left to right orientation is in the conventional direction of amino-terminus to carboxy-terminus. Further, it should be noted that a dash at the beginning or end of an amino acid residue sequence indicates either a peptide bond to a further sequence of one or more amino acid residues or a covalent bond to an end group. $NH_2$ at the C-terminus of a polypeptide is used to indicate that the carboxy terminus of the polypeptide is amidated.

CRF:CRF-BP: Designates CRF-BP when it is complexed (bound), either by hydrophobic, ionic, or covalent interactions, with CRF peptide.

CRF/CRF-BP: Designates the ratio of free CRF to free CRF-BP, e.g., CRF-BP not bound to CRF and vice versa, in a vascular fluid sample.

Homology: The term is used in its usual and well known sense of indicating correspondence between members in a sequence, e.g. either on an amino acid (AA) level or at the nucleotide level. For purposes of this application, by homologous is meant having at least about 70% correspondence, by substantially homologous is meant having a correspondence of at least about 80%, and by highly homologous is meant having a correspondence of at least about 90% or preferably about 95% or higher.

Isolated CRF-BP: Designates CRF-BP that is substantially free of other proteins or polypeptides, such as CRF, that are typically found associated with CRF-BP.

Peptide and Polypeptide: Polypeptide and peptide designates a linear series of amino acid residues connected one to the other by peptide bonds between the alpha-amino and alpha-carboxy groups of adjacent residues. The term polypeptide is used somewhat interchangeably with peptide but, unless otherwise limited, is generally also used to include the proteins described herein.

Protein: Protein is a term used herein to designate a linear series of about 50 or more amino acid residues connected one to the other as in a polypeptide.

Synthetic peptide: Refers to a chemically produced chain of amino acid residues, linked together by peptide bonds, that is free of naturally occurring proteins and fragments thereof.

The isolation of the CRF-BP protein was greatly complicated because of the fact that it had a finite shelf life, even at 4° C., because of two phenomena. Having been isolated from serum, the serum proteases remain in the partially purified material, and they continuously gradually decrease the amount of target protein while additional purification runs to attempt to increase that amount might be carried out. Moreover, it was found that CRF-BP has a natural tendency to aggregate, and aggregation causes the protein to precipitate and results in loss of its bioactivity. The greater the concentration of the protein, the greater is its tendency to aggregate, and it has not been possible to de-aggregate such CRF-BPs under normal physiological conditions. Moreover, it was not possible to freeze the partially purified extracts to prevent proteolytic degradation because freezing was found to substantially reduce bioactivity and increase aggregation.

An amount of the human 37 kD protein estimated to be about 100 picomoles was partially purified from human plasma using three successive hCRF-Sepharose affinity column separations, followed by gel filtration. By then using critical improvements in a known technique of micro-preparative SDS polyacrylamide gel electro-phoresis (PAGE)-in situ proteolysis described in Aebersold et al., *P.N.A.S.* 84, 6970-6974 (1987), sequence data of tryptic fragments was obtained. Briefly, this improved separation procedure produced a major band of the expected size of about 37 kD and a number of bands of impurities of higher and lower molecular weights. The resultant bands were transferred to nitrocellulose, and the major protein band corresponding to the binding protein was excised and then treated with trypsin in situ, using the general procedure described in Aebersold et al., supra. Only by incorporating improvements in the buffer solutions and using newly developed techniques that permitted tryptic digestion in only 30 microliters of volume was it possible to minimize contaminating products, created by trypsin autolysis, and thereby allow recovery from such small picomole quantities of protein. The different tryptic fragments were recovered from the supernatant and resolved by RP-HPLC; seven separate tryptic fragments were then subjected individually to Edman degradation to obtain the amino acid sequences thereof. In addition, N-terminus sequence analysis of the overall protein, following its purification by the aforementioned SDS gel electrophoresis step, was carried out by binding the separated bands to polyvinylidene difluoride filter material, excising the appropriate band, and then directly sequencing the pure material.

Following complete characterization of the clone as encoding a 322-residue precursor protein, it was possible to identify the positions of these fragments in the precursor protein. It is now known that these seven tryptic fragments which were first sequenced, constituted residues 30-45, residues 47-55, residues 112-119, residues 123-135, residues 152-162, residues 163-175, and residues 294-299 of the precursor human CRF-BP protein that is set forth hereinafter as SEQ ID NO:1. Following the sequencing of the seven tryptic fragments, two sets of degenerate oligonucleotide primers were made corresponding to sequences from tryptic fragment 30-45 and tryptic fragment 152-162. A first degenerate oligonucleotide primer was designed based upon residues 33-43 in the first tryptic fragment, (SEQ ID NO:5): GA(T/C)TA(T/C)GATCCNTT(T/C)(C/T)TN(C/T)TNTT (T/C)(T/A) (C/G)NGCNAAC. A second degenerate oligo primer was designed based upon residues 154-161 of the other tryptic fragment that was selected, (SEQ ID NO:6): CA(A/G)AA(T/C)GTNGCNATGATNTT(C/T)TTC.

DNA from a human adult liver cDNA library was used as a template in 35 cycles of the polymerase chain reaction (PCR) with 1 minute of denaturation at 94° C., 2 minutes of annealing at 45° C., and 3 minutes of extension at 72° C. The PCR products were analyzed on a 1% (w/v) TBE agarose gel; a 387 bp fragment was electroeluted into a 12M ammonium acetate solution using an IBI model UEA Bio-Rad electroeluter. The 387 PCR fragment was subcloned into the Sma I site of Bluescript KS vector, and nucleotide sequencing was then carried out using the Sanger dideoxy chain termination method using Sequenase (USB). The sequenced DNA fragment contained an open reading frame which also encoded tryptic fragments 47-55, 112-119, and 123-135, along with peptides corresponding to the oligonucleotide primers on the 5' and 3' ends.

The coding region from this PCR subclone was random-primed and then used to screen the original human liver cDNA library.

Duplicate nitrocellulose filters were hybridized in 50% formamide, 5 parts SSC buffer, 1 part Denhardt's solution, 0.1% SDS, 100 µg/ml sheared salmon sperm DNA and $^{32}P$ labelled insert ($1\times10^6$ cpm/ml) 42° C. for 18 hours. Filters were washed at 60° C. in 2×SSC. Two partial overlapping clones for the hCRF-BP coding region were isolated containing inserts 650 bp and 570 bp, respectively. The inserts were subcloned, sequenced and shown to contain partial cDNA sequences for the human CRF-BP.

A new library using adult human liver RNA was constructed in order to obtain full length cDNA clones. mRNA was isolated by guanidium isothiocynate-caesium chloride method and oligo dT chromatography. 10 µg mRNA was used for the λ-Zap II cloning system (Stratagene) which made a library with a $5\times10^6$ bases. $1\times10^6$ plaques were screened with inserts from the two partial, overlapping clones. Seven clones were identified, one of which contained a 1.8 kb insert with an open reading frame coding for a 322 amino acid protein which contained all of the amino acid sequences from the tryptic fragments of the purified hCRF-BP. The amino acid sequence of 322 residues, which includes what is believed to be a 24-residue signal sequence (as determined via N-terminal sequence analysis), is set forth in the Sequence Listing as SEQ ID NO:1. The nucleotide sequence and the encoded amino acid sequence from the clone are set forth as SEQ ID NO:2. Once one has the nucleic acid sequence of one mammalian species, it is a straightforward exercise to obtain homologous, naturally occurring variant sequences of other animal species, which will encode homologous binding proteins, as described hereinafter.

Based upon N-terminal sequencing of the purified hCRF-BP, it is determined that the mature protein begins at residue 25 (Tyr) and that the N-terminal 24-residues constitute a signal sequence, as represented hereinabove. A putative N-glycosylation site is found in the predicted sequence at Asn residue 204 (i.e. residue 180 of the 298-residue mature protein sequence), which is consistent with the presence of asparagine-linked sugar moieties in the native hCRF-BP. Analysis of the full length sequence for hydrophobicity, using the Kyte and Doolittle program, revealed a pattern of randomly dispersed hydrophobic and hydrophilic sections characteristic of a soluble protein. There are 10 interdispersed cysteine residues (excluding the 24-residue signal sequence) which suggests the potential presence of five intramolecular disulfide bonds. This is consistent with the experimental data that the reduced form of the purified hCRF-BP exhibits a higher apparent molecular weight, than does the non-reduced form, when run on an SDS gel—a characteristic of a protein containing disulfide bonds. It has now been determined that the first pair of Cys residues, i.e. $Cys^{36}$-$Cys^{57}$ of the mature protein, are linked to each other, as are the second pair, etc. through the fifth pair, i.e. $Cys^{253}$-$Cys^{294}$ of the mature protein.

The CRF peptide of the human species has the following amino acid sequence: H-Ser-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Glu-Ile-Ile- $NH_2$ (SEQ ID NO:7) which is the exact same 41 amino acid sequence as the CRF peptide of the rat species, from which fact homology between the critical regions of the binding proteins can be fairly predicted. mRNA from rat brain was screened for mRNA for CRF-BP, and the target mRNA was detected. Thereafter, a rat cortex cDNA library was screened, using the human cDNA as a hybridization probe, and several clones were isolated which hybridized thereto under what are well known in the art as high stringency conditions. One clone contained a 1.85 kb insert which was sequenced; it predicted a 322 amino acid precursor protein that is 84% identical to human CRF-BP. The deduced amino acid sequence of the rat species is set forth in the Sequence Listing as SEQ ID NO:3. The nucleotide sequence and the encoded amino acid sequence of the clone from which the sequence was deduced is set forth as SEQ ID NO:4. The nucleotide sequences encoding CRF-BPs of other species could be similarly obtained using appropriate libraries.

All ten of the cysteine residues and the putative N-glycosylation site appear at exactly the same residues in the rat sequence as in the human sequence; this conservation between the human and rat CRF-BPs suggests that these residues may play an important role in the structure/function of CRF-BP.

By cloning the gene encoding human CRF-BP, recombinant expression of this protein is made feasible, and, as a result, methods of treatment can be carried out by the peripheral administration of the recombinant protein. The protein can also be purified from human serum using the procedure described in Perkins et al., *J. Endocrinology*, 138, 149–157 (1993).

Recombinant hCRF-BP and rCRF-BP demonstrated bioactivity to inhibit CRF-induced ACTH release from primary rat pituitary cells in a competitive manner. The results of this experimental data show that the rat CRF-BP and the human CRF-BP are substantially equally effective in inhibiting CRF-induced ACTH release, which is not unexpected insofar as the two native CRF peptides have the exact same amino acid sequence. In these experiments, the conditioned media was placed on primary and carrier pituitary cell cultures using known techniques, as earlier described in Vale, W., et al., *Methods in Enzymology—Hormone Action-:Neuropeptides* (Academic Press) 124, 389–401 (1986). Varying concentrations of rCRF were added to the media, and the cultures were incubated for 3 hours. The media was then removed and assayed for ACTH by double antibody RIA (Diagnostic Products Corp.). As a result of these tests, it is considered that bioactivity of CRF is abolished as a result of binding between CRF and CRF-BPs; thus, it is considered that the CRF-BPs can be administered so as to treat hypertension thought to be caused by elevated CRF levels as in the case of pregnancy-induced hypertension. IV administration of 50 µg of CRF-BP to male rats, followed in one minute by 5 µg of r/hCRF, showed no rise in plasma ACTH over 30 minutes, proving the effectiveness of CRF-BP administration in vivo.

Analyses of the human and rat CRF-BPs show that the recombinantly produced binding proteins (see Potter et al. supra) have the same high affinity for r/hCRF as that exhibited by the purified human CRF-BP ($K_d$=0.1 ±0.2 nM). However, the experimental data shows that the recombinant CRF-BPs bind ovine CRF with a much lower affinity. This indicates a difference between the binding protein and the pituitary CRF receptor which does not significantly distinguish between binding to r/hCRF and binding to oCRF. Moreover, it appears that the CRF-BPs BPs have as high or higher affinity for r/hCRF than CRF receptors have. Generally, a protein having a $k_D$ of about 5 nanomolar or below in a standard binding assay would be considered to bind CRF with high affinity.

CRF and its target cell receptors are broadly distributed throughout the central nervous system and in a number of peripheral tissues, including placenta, adrenal, sympathetic ganglia, lymphocytes, gastrointestinal tract, pancreas and gonads. Generally, CRF is produced and acts in a trans-synaptic, paracrine or neuroendocrine fashion. It appears that the plasma CRF-BP provides a mechanism to protect human beings from hormonally significant concentrations of CRF and thereby protects the integrity of this restricted system especially during pregnancy. The presence of mRNA for CRF-BP in the brains of primates and rats suggests that this protein co-localizes to some CRF pathways and modulates the neural roles of the neuropeptide CRF.

The availability of such mammalian CRF-BP proteins permits their use to bind to or complex with CRF and thereby neutralize or modulate the biological activity of CRF, and these proteins should be useful in the treatment of conditions which are caused by an overabundance of CRF, for example, during chronic stress or in the presence of a CRF-secreting tumor. Furthermore, CRF-BP's as well as fragments thereof can be used to bind, sequester and/or detect CRF either by themselves or in conjunction with an antibody to CRF, using "two-site" methodology. The binding ability of CRF-BPs also allows them to be used in an affinity chromatography column to purify hCRF or homologues of CRF. Moreover, administration of substantially pure polyclonal or monoclonal antibodies to CRF-BP have potential therapeutic applications to treat cases where it is desired to counteract the binding effect of CRF-BPs.

Substantially pure recombinant CRF-BP protein can be routinely obtained having significantly higher purity than naturally occurring CRF-BP that is present in crude extracts from mammalian serum. Naturally occurring CRF-BP proteins constitute only minor constituents of normal mammalian serum, being present in only very impure form, relative to other native proteins also present. Because of the work involved and the low concentration in plasma, it would be impractical to prepare CRF-BP by purification from natural sources. Recombinant DNA techniques, for example, can be used to generate organisms or cell lines that produce the heterologous protein in significantly higher proportions, relative to total protein, in the cellular material and/or the secretions thereof—as compared to the proportions at which native CRF-BP is present. Because the starting material from which such synthetic recombinant CRF-BP proteins are isolated is from media which is essentially free of protein contaminants (serum free media) and has a substantially greater concentration of the heterologous protein, available purification techniques can fairly simply produce more highly purified CRF-BP preparations in relatively copious amounts. Using appropriate isolation techniques, it is possible to routinely obtain CRF-BP proteins which are at least about 98% pure (by weight of total proteins) and which is herein referred to as substantially pure.

When coupled to a carrier to form what is known in the art as a carrier-hapten conjugate, a CRF-BP polypeptide is capable of inducing antibodies that immunoreact with CRF-BP. In view of the well-established principle of immunologic cross-reactivity, the present invention therefore contemplates antigenically related variants of such polypeptides. An "antigenically related variant" is a subject polypeptide that is capable of inducing antibody molecules that immunoreact with the CRF-BP polypeptides described herein.

As used herein, the phrase "CRF-BP polypeptide" refers to a polypeptide whose amino acid residue sequence corresponds, and preferably is identical to a full length mammalian CRF-BP protein molecule or a fragment thereof. The term "fragment" refers to any subject polypeptide having an amino acid residue sequence shorter than that of the mature protein whose amino acid residue sequence is shown herein, e.g., as in SEQ ID NO:1 and NO:3. Fragments can be produced either synthetically, recombinantly, or by proteolytic cleavage as described herein.

The entire recombinant mature protein can be used as an antigen, if desired, to obtain an antibody which binds to CRF-BP; however, in a preferred embodiment, a CRF-BP polypeptide fragment for use as an antigen comprises no more than about 60 amino acid residues and preferably no more than about 32 amino acid residues, for example, the 32 N-terminal or the 32 C-terminal residues of the mature protein. The antigen preferably includes an amino acid residue sequence, selected from the mature protein of either SEQ ID NO:1 or SEQ ID NO:3, of at least 5 amino acid residues, more preferably at least 10 amino acid residues, still more preferably at least about 15 amino acid residues, and most preferably of about 20 residues. The polypeptide antigen should include a native epitope of CRF-BP that is exposed in the native protein so that an anti-CRF-BP antibody will have the ability to immunoreact therewith. Examples of specific polypeptide fragments which are advantageously employed include those which appear at the N-terminus or the C-terminus of the mature protein, for example residues 1-21 i.e., Tyr-Leu-Glu-Leu-Arg-Glu-Ala-Ala-Asp-Tyr-Asp-Pro-Phe-Leu-Leu-Phe-Ser-Ala-Asn-Leu-Lys, or residues 1-16 thereof (which are amino acid residues 25-40 of the precursor protein of SEQ ID NO:1); alternatively the first 18 or 24 or 30 N-terminal residues may be used. Preferably, a CRF-BP polypeptide for use in an assay or as an antigen should be further characterized by its ability to continue to immunologically mimic an epitope (antigenic determinant) exhibited by CRF-BP when bound to r/hCRF in a CRF:CRF-BP complex.

As used herein, the phrase "immunologically mimic" in its various grammatical forms refers to the ability of such a CRF-BP polypeptide to immunoreact with an antibody of the present invention that recognizes a native epitope of CRF-BP as defined herein. A suitable method for mapping CRF-BP epitopes for a variety of antibodies, specifically monoclonal antibodies, is described in Mehra et al., PNAS, 83:7013–7017 (1986). It should be understood that a subject polypeptide need not be identical to the amino acid residue sequence of CRF-BP, so long as it includes the required sequence and is able to immunoreact with antibodies of the present invention.

Just as for the subject CRF-BP protein of the present invention, a subject polypeptide includes any analog, fragment or chemical derivative of a polypeptide whose amino acid residue sequence is shown herein so long as the polypeptide is capable of immunologically mimicking a CRF-BP native epitope or is capable of exhibiting another biological property of CRF-BP, such as binding to CRF. Therefore, such a polypeptide can include changes, substitutions, insertions and/or deletions which are advantageous.

The term "analog" includes any polypeptide having an amino acid residue sequence substantially identical to a sequence specifically shown herein in which one or more residues have been conservatively substituted with a functionally similar residue and which displays the ability to mimic CRF-BP as described herein. Examples of conservative substitutions include: the substitution of one non-polar (hydrophobic) residue, such as isoleucine, valine, leucine or methionine for another; the substitution of one polar (hydrophilic) residue for another, such as between arginine and lysine, between glutamine and asparagine, between glycine and serine; the substitution of one basic residue such as lysine, arginine or histidine for another; and the substitution of one acidic residue, such as aspartic acid or glutamic acid for the other. The phrase "conservative substitution" also includes the use of a chemically derivatized residue in place of a non-derivatized residue provided that such polypeptide displays the requisite binding activity.

"Chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to from O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include those having one or more additions and/or deletions of residues relative to the sequence of a polypeptide whose sequence is shown herein, so long as the requisite activity is maintained.

When a polypeptide of the present invention has a variant sequence that is not identical to the sequence of a CRF-BP, one or more conservative or non-conservative substitutions have been made. The percentage of amino acid residues that are substituted is usually no more than about 30 number percent, more usually no more than 20 number percent, and preferably no more than 10 number percent of a native CRF-BP. When additional residues have been added at either terminus for the purpose of providing a "linker" by which the polypeptides of this invention can be conveniently affixed to a label or solid matrix, or carrier, the linker residues are selected such that they do not form a CRF-BP epitope, i.e., are not similar in structure to the CRF-BP. Labels, solid matrices, and carriers that can be used with the polypeptides of this invention are described hereinbelow.

Amino acid residue linkers include at least one residue up to 40 or more residues (more often they comprise 1 to 10 residues), but do not form CRF-BP epitopes. Typical amino acid residues used for linking are tyrosine, cysteine, lysine, glutamic acid and aspartic acid. In addition, a subject polypeptide can differ in sequence, unless otherwise specified, from the natural sequence of CRF-BP by modification of the sequence by N-terminal acylation e.g., acetylation or thioglycolic acid amidation, and by C-terminal amidation, e.g., with ammonia, methylamine, and the like.

Any polypeptide of the present invention may be administered in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di-, and tri-alkyl and -aryl amines (e.g., triethylamine, diisopropyl amine, methyl amine, dimethyl amine and the like) and optionally substituted ethanolamines (e.g., ethanolamine, diethanolamine, and the like).

CRF-BP polypeptide fragments can be synthesized by any of the techniques that are known to those skilled in the polypeptide art, including recombinant DNA techniques. Synthetic chemistry techniques, such as a solid-phase Merrifield-type synthesis, are preferred for producing polypeptide fragments for reasons of purity, antigenic specificity, freedom from undesired side products, ease of production and the like.

A CRF-BP polypeptide can be used, inter alia, in the diagnostic methods and systems of the present invention to detect the level of CRF-BP present in a body sample, to detect the ratio of CRF/CRF-BP levels in a body sample, or can be used to prepare an inoculum as described herein for the preparation of antibodies that immunoreact with native epitopes on CRF-BP.

In addition, certain CRF-BP polypeptides of this invention which bind to CRF can be used in the therapeutic methods of the present invention to inhibit the CRF-induced ACTH release and decrease the level of ACTH in a patient.

Antibodies (Abs) to CRF-BP or its fragments, of either monoclonal or polyclonal form, are produced using techniques well known in the art. Antibodies which are effective to counteract the effects of CRF-BP can be elicited using the methods described herein. The term "antibody" or "antibody material" in its various grammatical forms is used herein as a collective noun that refers to a population of immunoglobulin molecules and/or immunologically active portions of immunoglobulin molecules, i.e., molecules that contain an antibody combining site or paratope. An "antibody combining site" is that structural portion of an antibody molecule comprised of heavy and light chain variable and hypervariable regions that specifically binds antigen. The phrase "antibody molecule" in its various grammatical forms as used herein contemplates both an intact immunoglobulin molecule and an immunologically active portion of an immunoglobulin molecule.

Exemplary antibody molecules for use in the diagnostic methods and systems of the present invention are intact immunoglobulin molecules, substantially intact immunoglobulin molecules and those portions of an immunoglobulin molecule that contain the paratope, including those portions known in the art as Fab, Fab', $F(ab')_2$ and F(v). Fab and $F(ab')_2$ portions of antibodies are prepared by the proteolytic reaction of papain and pepsin, respectively, on substantially intact antibodies by methods that are well known, see, for example, U.S. Pat. No. 4,342,566. Fab' antibody portions are also well known and are produced from $F(ab')_2$ portions followed by reduction of the disulfide bonds linking the two heavy chain portions as with mercaptoethanol, and followed by alkylation of the resulting protein mercaptan with a reagent such as iodoacetamide. An antibody which contains intact antibody molecules is preferred.

In one embodiment, an anti-CRF-BP antibody is provided that is capable of immunoreacting with isolated, substantially pure CRF-BP.

In another embodiment, an anti-CRF-BP antibody is provided that immunoreacts substantially only with isolated, substantially pure CRF-BP, and that is substantially free of antibody molecules that immunoreact either with any other non-CRF-BP polypeptide, particularly CRF, or with impurities as might be contained in an impure protein extract.

In still another embodiment, an anti-CRF-BP antibody is provided that is capable of immunoreacting both with isolated CRF-BP and with CRF-BP bound to CRF (CRF:CRF-BP complex); it can be substantially free of antibody molecules that immunoreact either with a non-CRF-BP polypeptide, such as CRF, or with impurities as might be contained in an impure protein extract.

In yet another embodiment, an anti-CRF-BP antibody is provided that is raised against a fragment of the mature protein of SEQ ID NO:1 or NO:3 at least about 15 residues in length and which immunoreacts with free or isolated CRF-BP, and with CRF:CRF-BP complex, by specifically binding thereto, and which antibody will not immunoreact with a different polypeptide fragment of SEQ ID NO:1 or NO:3 that is not present in the sequence of the specific fragment used as the immunogen. For example, a specific N-terminal fragment such as CRF-BP(1-21) or CRF-BP(1-16), i.e. amino acid residues 25-40 of the precursor protein of SEQ ID NO:1, might be used as the immunogen for raising an anti-CRF-BP polyclonal antibody, which is then referred to as anti-CRF-BP(1-16), based upon the sequence of the mature protein. The anti-CRF-BP(1-16) antibody that results is directed to, i.e. specifically binds, an epitope in the 16-residue N-terminal region and does not immunoreact with polypeptide fragments of at least 5 residues lying between residues 17 and 298 of the mature protein. Other fragments which might be used are those at the C-terminus, such as the last about 32 residues, i.e. those beyond residue 266 of the mature protein, for example the last 15 or 20 or 25 residues, e.g. CRF-BP(274-298), or CRF-BP(283-298).

In a further embodiment, an anti-CRF-BP antibody is provided which only immunoreacts with free CRF-BP, e.g., CRF-BP that is not complexed with CRF, and does not immunoreact with CRF:CRF-BP complex. Such antibodies (Abs) might bind to a CRF-BP epitope that becomes blocked or inhibited when CRF is bound to CRF-BP. Certain internal sequences of SEQ ID NO:1 or NO:3 may be employed to obtain antibody that will only bind free CRF-BP and not bind CRF-BP complexed with CRF. More specifically, such antibodies may be provided by using, as an immunogen, a peptide which is contained in the sequence of residues 159 to 181 of the mature protein (see SEQ ID NO:2). It is a straightforward matter to raise Abs against peptide segments of CRF-BP about 5 to 15 residues in length and then test them to determine if they bond to (a) free CRF-BP and/or CRF:CRF-BP complex, or if they prevent CRF-BP from binding its ligand. Once the CRF binding site in CRF-BP is completely determined, peptides constituting that site can be used in affinity chromatography to selectively remove from a polyclonal Ab made using the complete molecule Abs which recognize that site and therefore only recognize free CRF-BP.

In one particular aspect, an anti-CRF-BP antibody is provided that is substantially free of antibody molecules that would immunoreact with CRF-BP at a location that inhibits or disturbs the binding of CRF to CRF-BP. Such antibody may bind to a CRF-BP epitope that is not blocked or inhibited when CRF is bound to CRF-BP; examples of such antibodies include those made with immunogens in the form of amino acid sequences from the vicinity of the N-terminus, e.g. residues 1-16, 1-32 or 1-35, or of the C-terminus, e.g. residues 267-298, 241-298 or 283-298 of the mature protein, which is so numbered adjacent to SEQ ID NO:2. As another example, the remainder of a polyclonal Ab which was purified by selective removal of Abs that recognize the binding site, as described above, could be used for this purpose.

Antibody immunoreactivity with antigens which contain CRF-BP or fragments can be measured by a variety of straightforward immunological assays known in the art. Exemplary immunoreaction of an anti-CRF-BP antibody with a CNBr fragment of CRF-BP is described hereinafter. Direct binding with CRF:CRF-BP complex, with isolated or recombinant CRF-BP, and with CRF-BP polypeptide fragments can be assayed using the methods described hereinafter or by others known in this art. Thus, it is a straightforward exercise to determine the effectiveness of any antibody made against a peptide fragment of SEQ ID NO:1 to specifically bind to free CRF-BP and CRF:CRF-BP complex, and such antibodies can easily be raised now that the amino acid sequence of hCRF-BP is known.

An antibody of the present invention is typically produced by immunizing a mammal with an inoculum containing a CRF-BP protein or polypeptide fragment thereof to thereby induce in the mammal antibody molecules having immunospecificity for CRF-BP or polypeptide fragment thereof. For example, antibodies raised in rabbits against a synthetic peptide fragment may recognize the synthetic peptide and CRF-BP on an equimolar basis, and preferably, they should also be capable of inhibiting the activity of the native protein in vitro. Antibodies to CRF-BP may be obtained, for example, by immunizing three month old male and female white New Zealand rabbits with the synthetic peptide fragment to which Tyr has been added at the N-terminus or C-terminus in order to couple it as an antigen, to BSA by a bisdiazotized benzidine(BDB) linkage, e.g., by reaction for 2 hours at 4° C. The reaction mixture is dialyzed to remove low molecular weight material, and the retentate is frozen in liquid nitrogen and stored at −20° C. Animals are immunized with the equivalent of 1 mg of the peptide antigen according to the procedure of Benoit et al. *P.N.A.S.* USA, 79, 917–921 (1982). At four week intervals, the animals are boosted by injections of 200 μg of the antigen and bled ten to fourteen days later. After the third boost, antiserum is examined for its capacity to bind radioiodinated antigen peptide prepared by the chloramine-T method and then purified by CMC-ion exchange column chromatography. The antibody molecules are then collected from the mammal and isolated to the extent desired by well known techniques such as, for example, by using DEAE Sephadex to obtain the IgG fraction.

To enhance the specificity of the antibody, the antibodies may be purified by immunoaffinity chromatography using solid phase-affixed immunizing polypeptide. The antibody is contacted with the solid phase-affixed immunizing polypeptide for a period of time sufficient for the polypeptide to immunoreact with the antibody molecules to form a solid phase-affixed immunocomplex. The bound antibodies are separated from the complex by standard techniques.

A radioimmunoassay is established with the antisera and serum from subsequent bleeds from the same rabbits. Effective antibodies may recognize the native protein on an equimolar basis as compared to the synthetic peptide antigen. In one preferred embodiment, these antibodies are capable of at least partially neutralizing the biological activity of CRF-BP, and substantially all such activity can be neutralized when higher amounts of antibodies are used.

The antibody so produced can be used, inter alia, in diagnostic methods and systems to detect the level of CRF-BP present in a mammalian, preferably human, body sample, or to detect the ratio of CRF/CRF-BP levels in a vascular fluid sample, as described in the examples set forth hereinafter. The anti-CRF-BP antibodies can also be used for the immunoaffinity or affinity chromatography purification of CRF-BP from serum or from other biological materials. In addition, an anti-CRF-BP antibody can be used in human therapeutic methods to neutralize or modulate the effect of CRF-BP, increase the level of free CRF (e.g., CRF not bound by CRF-BP), increase CRF-induced ACTH release and/or increase the level of ACTH-induced glucocorticoids in a patient.

The word "inoculum" in its various grammatical forms is used herein to describe a composition containing a CRF-BP protein or polypeptide fragment thereof as an active ingredient used for the preparation of the antibodies against CRF-BP or a polypeptide fragment thereof. When a polypeptide is used in an inoculum to induce antibodies, it is to be understood that the polypeptide can be used in various embodiments, e.g., alone or linked to a carrier as a conjugate, or as a polypeptide polymer. However, for ease of expression and in context of a polypeptide inoculum, the various embodiments of the polypeptides are collectively referred to herein by the term "polypeptide" or "peptide immunogen," and their various grammatical forms. For a polypeptide that contains fewer than about 35 amino acid residues, it may be preferable to use the peptide bound to a carrier for the purpose of inducing the production of antibodies.

One or more additional amino acid residues can be added to the amino- or carboxy-termini of the polypeptide to assist in binding the polypeptide to such a carrier. Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, dialdehydes such as glutaraldehyde, Klipstein et al., *J. Infect. Dis.*, 147:318–326 (1983) and the like, or the use of carbodiimide technology as in the use of a water-soluble carbodiimide to form amide links to the carrier. For a review of protein conjugation or coupling through activated functional groups, see Aurameas, et al., *Scand. J. Immunol.*, 1:7–23 (1978). Useful carriers are well known in the art and are generally proteins themselves. Exemplary of such carriers are keyhole limpet hemocyanin(KLH), edestin, thyroglobulin, albumins such as bovine serum albumin (BSA) and human serum albumin (HSA), red blood cells such as sheep erythrocytes (SRBC), tetanus toxoid, cholera toxoid, as well as polyamino acids such as poly (D-lysine: D-glutamic acid), and the like. The choice of carrier is more dependent upon the ultimate use of the inoculum and is based upon criteria not particularly involved in the present invention. For example, a carrier that does not generate an untoward reaction in the particular animal to be inoculated should be selected.

The inoculum should contain an effective, immunogenic amount of a CRF-BP polypeptide, typically as a conjugate of a CRF-BP fragment linked to a carrier. The effective amount of polypeptide per unit dose sufficient to induce an immune response to the immunizing polypeptide depends, among other things, on the species of animal inoculated, the body weight of the animal and the chosen inoculation regimen as is well known in the art. Inocula typically contain about 10 micrograms to about 500 milligrams of polypeptide per inoculation dose, and preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent, i.e., carrier or vehicle. The specifications for the novel unit dose of an inoculum are dictated by and are directly dependent on (a) the unique characteristics of the active material and the particular immunologic effect to be achieved, and (b) the limitations inherent in the art of compounding such active material for immunologic use in animals.

Inocula are typically prepared from the dried solid polypeptide-conjugate by dispersing the polypeptide-conjugate in a physiologically tolerable (acceptable) diluent, such as water, saline or phosphate-buffered saline to form an aqueous composition.

The techniques of polypeptide conjugation or coupling through activated functional groups presently known in the art are particularly applicable. See, for example, Aurameas et al., *Scand.*, supra, and U.S. Pat. Nos. 4,493,795, 3,791, 932, and 3,839,153. In addition, a site-directed coupling reaction can be carried out so that any loss of activity due to polypeptide orientation after coupling can be minimized, see, for example, Rodwell et al., *Biotech.*, 3:889–894 (1985), and U.S. Pat. No. 4,671,958.

One or more additional amino acid residues may be added to the amino- or carboxy-termini of the polypeptide to assist in binding the polypeptide to form a conjugate. Cysteine residues, usually added at the carboxy-terminus of the polypeptide, have been found to be particularly useful for forming conjugates via disulfide bonds, but other methods well-known in the art for preparing conjugates may be used.

The phrase "monoclonal antibody" in its various grammatical forms refers to a population of antibody molecules that contain only one species of antibody combining site capable of immunoreacting with a particular epitope. A monoclonal antibody typically displays a binding affinity for a single epitope with which it immunoreacts; however, a monoclonal antibody may be a molecule having a plurality of antibody combining sites, each immunospecific for a different epitope, e.g., a bispecific monoclonal antibody.

A preferred monoclonal antibody (i.e. subject monoclonal antibody) displays a ratio of immunoreactivities for native CRF-BP and a subject CRF-BP polypeptide fragment in the range of about 1:5 to about 5:1, preferably from about 1:2.5 to about 2.5:1, and more preferably from about 1.5:1 to about 1:1.5, when the immunoreactivities are determined using molar equivalents of CRF-BP and the polypeptide fragment.

As used herein, the term "immunoreactivity" in its various grammatical forms refers to the concentration of antigen required to achieve a 50% inhibition of the immunoreaction between a given amount of the antibody and a given amount of CRF-BP. That is, immunoreactivity is the concentration of antigen required to achieve a $B/B_o$ value of 0.5, where $B_o$ is the maximum amount of antibody bound in the absence of competing antigen and B is the amount of antibody bound in the presence of competing antigen, and both $B_o$ and B have been adjusted for background, see Rodbard, *Clin. Chem.*, 20:1255–1270 (1974).

A more preferable monoclonal antibody of the present invention has identical (indistinguishable) affinities for native CRF-BP and a particular CRF-BP polypeptide fragment. That is, such a preferred monoclonal antibody has an affinity for CRF-BP and also an affinity for a CRF-BP polypeptide fragment which are indistinguishable (equivalent) by statistical analysis to within a confidence limit of p<0.1, preferably p<0.05, more preferably p <0.01. Such monoclonal antibodies can be produced in a straightforward manner using selected peptide fragments of SEQ ID NO:1 as antigens as is well known in this art.

Methods for determining the affinity of a monoclonal antibody for antigens and for comparing those affinities for equivalence are well known in the art, see, for example, Muller, *J. Immunol. Meth.*, 34:345–352 (1980) and Sokal et al., *Biometry*, W. H. Freeman & Co., (1981). A preferred method for determining monoclonal antibody affinity is by equilibrium competitive inhibition analysis. In that method, the ability of CRF-BP to compete with itself for binding to the monoclonal antibody being characterized is determined and compared for equivalence to the ability of a particular CRF-BP polypeptide fragment to compete with CRF-BP for binding to the monoclonal antibody being characterized, see Tsao et al., *J Biol. Chem.*, 257:15222–15228 (1982).

For example, determining whether or not the affinities displayed by a monoclonal antibody, or a polyclonal antibody described previously, for CRF-BP and a CRF-BP polypeptide fragment are identical (indistinguishable) can be performed in the following manner:

(a) The percent of a known amount of antibody bound to solid-phase CRF-BP in the presence of a CRF-BP polypeptide fragment present as a liquid-phase competitor is determined at various known competitor concentrations. The logit transformation of each percent bound determination is then plotted against competitor (liquid-phase polypeptide) concentration. [Logit $(Y)=log_e(Y/1-Y)$ where Y is the percent binding of antibody in the presence of a given amount of competitor.]

(b) Using the same amount of antibody as in step (a), the percent of antibody bound to solid-phase CRF-BP in the presence of CRF-BP present as liquid-phase competitor is determined at the same concentration as the competitor in step (a). The logit transformation of each percent bound is then plotted against competitor (liquid-phase CRF-BP) concentration.

(c) Linear regression analysis is performed on each of the plots obtained in steps (a) and (b) to obtain their respective slopes.

(d) The slopes obtained for CRF-BP and the slope obtained for a CRF-BP polypeptide fragment are then compared using a test for equality of slopes such as that described by Sokal et al., supra, p. 485, Box 14.5.

A monoclonal antibody is typically composed of antibodies produced by clones of a single cell called a hybridoma that secretes (produces) but one kind of antibody molecule. The hybridoma cell is formed by fusing an antibody-producing cell and a myeloma or other self-perpetuating cell line. The preparation of such antibodies was first described by Kohler and Milstein, *Nature*, 256:495–497 (1975). Hybridoma supernates so prepared can be screened for the presence of antibody molecules that immunoreact with CRF-BP protein or polypeptide fragment thereof, or for inhibition of binding to CRF by the CRF-BP protein or polypeptide fragments thereof.

Briefly, to form the hybridoma from which a monoclonal antibody composition of interest is produced, a myeloma or other self-perpetuating cell line is fused with lymphocytes obtained from the spleen of a mammal hyperimmunized with a CRF-BP antigen, such as a CRF-BP protein or a CRF-BP polypeptide fragment. Polypeptide-induced hybridoma technology is described by Niman et al., *Proc. Natl. Sci., U.S.A.*, 80:4949–4953 (1983).

It is preferred that the myeloma cell line used to prepare a hybridoma be from the same species or subgenus, e.g., rodent, as the lymphocytes. Typically, a mouse of the strain 129 ClX$^+$is the preferred mammal. Suitable mouse myelomas for use in the present invention include the hypoxanthine-aminopterin-Sp/2/0-Ag14 that are available from the American Type Culture Collection (ATCC), Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are identified using the radioimmunoassay (RIA) and the enzyme-linked immunosorbent assay (ELISA) described in examples hereinafter.

A monoclonal antibody of the present invention can also be produced by initiating a monoclonal hybridoma culture comprising a nutrient medium containing a hybridoma that secretes antibody molecules of the appropriate CRF-BP protein or polypeptide fragment specificity. The culture is maintained under conditions and for a time period sufficient for the hybridoma to secrete the antibody molecules into the medium. The antibody-containing medium is then collected, and the antibody molecules can then be purified by well known techniques.

Media useful for the preparation of these compositions are both well known in the art and commercially available; they include synthetic culture media, inbred mice and the like. An exemplary synthetic medium is Dulbecco's minimal essential medium (DMEM; Dulbecco et al., *Virol.*, 8:396 (1959)) supplemented with 4.5 gm/1 glucose, 20 mm glutamine, and 20% fetal calf serum. An exemplary inbred mouse strain is the Balb/c.

The monoclonal antibodies of this invention can be used in the same manner as disclosed herein for polyclonal antibodies. For example, a monoclonal antibody can be used in the therapeutic and diagnostic methods and systems disclosed herein where formation of a CRF-BP-containing immunoreaction product is desired. It should be noted that hybridoma ATCC 1580 can be used, as is well known in the art, to produce other immortal cell lines that produce a subject monoclonal antibody.

Other methods of producing a monoclonal antibody, a hybridoma cell, or a hybridoma cell culture are also well known, see, for example, the method of isolating monoclonal antibodies from an immunological repertoire as described by Sastry et al., *Proc. Natl. Acad. Sci.*, 86:5728–5732 (1989); and Huse et al., *Science*, 246:1275–1281 (1981). Also contemplated by this invention is the hybridoma cell line and cultures containing a hybridoma cell line that produce such a monoclonal antibody.

The present invention also provides a diagnostic system, preferably in kit form, for assaying for the presence of CRF-BP protein, CRF-BP polypeptide fragments, or CRF peptide in a fluid sample and which can assay for the ratio of CRF to CRF-BP. A suitable diagnostic system includes, in an amount sufficient for at least one assay, a subject CRF-BP protein or polypeptide fragment thereof and/or a subject antibody as a separately packaged immunochemical reagent. Instructions for use of the packaged reagent are also typically included. "Instructions for use" typically include a tangible expression describing the reagent concentration or at least one assay method parameter, such as the relative amounts of reagent and sample to be admixed, maintenance time periods for reagent/sample admixtures, temperature, buffer conditions and the like.

In one embodiment, a diagnostic system for assaying for the presence or quantity of CRF-BP in a vascular fluid sample, such as blood, plasma, or serum, comprises a package containing at least one CRF-BP protein or polypeptide fragment thereof of this invention. In addition, a diagnostic system containing at least one CRF-BP, or polypeptide fragment thereof, and appropriate antibodies can be used to detect the level of CRF peptide present in a vascular fluid sample.

In another embodiment, a diagnostic system of the present invention for assaying for the presence or amount of CRF-BP or a CRF-BP polypeptide in a sample includes an anti-CRF-BP antibody composition of this invention.

In yet another embodiment, a diagnostic system of the present invention for assaying for the presence or amount of CRF-BP or a CRF-BP polypeptide in a sample contains at least one CRF-BP, or polypeptide fragment thereof, and an anti-CRF-BP antibody composition of this invention. An exemplary diagnostic system is described hereinafter in one of the examples.

In one preferred embodiment, a diagnostic system of the present invention further includes a label or indicating means capable of signaling the formation of an immunocomplex containing a protein, polypeptide, or antibody molecule of the present invention. The word "complex" as used herein refers to the product of a specific binding reaction such as an antibody-antigen, receptor-ligand, or protein-protein reaction. Exemplary complexes are immunoreaction products and CRF:CRF-BP complexes.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide fragment, or antibody molecule that is part of an antibody or monoclonal antibody composition of the present invention, or used separately. These atoms or molecules can be used alone or in conjunction with additional reagents. Such labels are themselves well-known in clinical diagnostic chemistry and constitute a part of this invention only insofar as they are utilized with otherwise novel proteins, methods, and/or systems.

The label or indicating means can be a fluorescent labeling agent that chemically binds to antibodies without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamine-1-naphthalenesulfonyl chloride (DANSC), tetramethylrhodamine isothiocyanate (TRITC), lissamine, rhodamine 8200 sulphonyl chloride (RB-200-SC) and the like. A description of immunofluorescence analysis techniques is found in DeLuca, "Immunofluorescence Analysis", in Antibody As a Tool, Marchalonis et al., eds., John Wiley & Sons, Ltd., pp. 189–231 (1982), which is incorporated herein by reference.

In certain preferred embodiments, the indicating means is an enzyme, such as horseradish peroxidase (HRP), glucose oxidase or the like. In such cases where the principal indicating means is an enzyme, such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2,'-azino-di-(3-ethyl-benzthiazoline-G-sulfonic acid) (ABTS).

Radioactive elements are particularly useful labeling agents and are used illustratively herein. An exemplary radiolabeling agent is a radioactive element that produces gamma ray emissions. Elements which themselves emit gamma rays, such as $^{125}I$, $^{124}I$, $^{126}I$, $^{131}I$ and $^{51}Cr$, represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such as $^{111}$indium or $^3H$.

The linking of labels, i.e., labeling for antibodies, polypeptides and proteins, is well known in the art. For instance, antibody molecules produced by a hybridoma can be labeled by metabolic incorporation of radioisotope-containing amino acids provided as a component in the culture medium. See, for example, Galfre et al., Meth. Enzymol., 73:3–46 (1981). The techniques of protein conjugation or coupling through activated functional groups are particularly applicable. See, for example, Aurameas et al., Scand. J. Immunol., Vol. 8, Suppl. 7:7–23 (1978), Rodwell et al., Biotech., 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules (e.g., anti-Ig antibodies), complement proteins or fragments thereof, S. aureus protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits can be used in an "ELISA" format to detect the quantity of CRF, CRF-BP, or CRF:CRF-BP complex in a vascular fluid sample such as blood, serum, or plasma. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of Basic and Clinical Immunology by D. P. Sites et al., published by Lange Medical Publications of Los Altos, Calif. in 1982 and in U.S. Pat. No. 3,654,090, U.S. Pat. No. 3,850,752; and U.S. Pat. No. 4,016,043.

Thus, in preferred embodiments, CRF-BP protein, a CRF-BP polypeptide fragment thereof, a polyclonal anti-CRF-BP antibody, or a monoclonal anti-CRF-BP antibody is affixed to a solid matrix to form a solid support that comprises a package in the subject diagnostic systems. A reagent is typically affixed to a solid matrix by adsorption from an aqueous medium although other modes of affixation applicable to proteins and polypeptides, as well known to those skilled in this art, can be used.

Useful solid matrices are also well known in the art. Such materials are water-insoluble and include cross-linked dextran available from Pharmacia Fine Chemicals (Piscataway, N.J.); agarose; beads of polystyrene about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems. The term "package" refers to a solid matrix or material, such as glass, plastic (e.g., polyethylene, polypropylene and polycarbonate), paper, foil and the like, capable of holding within fixed limits a diagnostic reagent such a protein, polypeptide fragment, antibody or monoclonal antibody of the present invention. Thus, for example, a package can be a bottle, vial, plastic and plastic-foil laminated envelope or the like container used to contain a contemplated diagnostic reagent or it can be a microtiter plate well to which microgram quantities of a contemplated diagnostic reagent have been operatively affixed, i.e., linked so as to be capable of being immunologically bound by an antibody or polypeptide to be detected.

In normal healthy individuals, the levels of CRF-BP are about 50 to 300 nanograms per milliliter, whereas the levels of CRF can vary from 1 to 28 picograms per milliliter. Thus, the ratio of CRF/CRF-BP in normal healthy pregnant women in the second trimester and about the first month of the third trimester of pregnancy is generally such that the molar concentration of CRF-BP is about 1000 to about 400 times the molar concentration of CRF. The average level of CRF-BP is about 20 nanomoles per liter in normal individuals, varying from about 10 to 40 nM/L. However, during the last trimester of pregnancy, it has been found that the level of binding protein drops significantly, particularly in the last about 6 weeks, and there is a tendency for CRF levels to increase. When CRF levels prematurely rise and CRF-BP levels fall, this differential becomes even more pronounced, and it is believed it may well cause pregnancy-induced hypertension when it takes place in the second trimester or at an early stage in the third trimester. Such a change in the ratio of CRF to CRF-BP (CRF/CRF-BP), for example changes in which the concentration of CRF-BP prematurely falls below about 250 times that of CRF, can be used to predict the possibility or increased risk of premature labor, and thereafter pre-term delivery, which can then be avoided, e.g. by treating accordingly by administering CRF-BP. It is also believed that it is important to monitor this ratio because there are instances where the CRF levels could remain normal, yet a pathological problem or pre-term delivery could occur because the CRF-BP level drops. Alternatively, the ratio is also indicative of situations where post-term delivery is very likely to occur.

Thus, by monitoring the CRF/CRF-BP ratio, such an abnormal increase which is indicative of a potential pathological problem in pregnancy and/or increased risk of pre-term delivery can be detected at an early stage. Because normal hypertension is now believed to be either caused by or accompanied by a higher CRF/CRF-BP ratio than normal, monitoring the CRF/CRF-BP ratio allows the prediction of particular patients who are predisposed to such diseases and permits therapeutic intervention—as for example by administering dosages of CRF-BP protein or polypeptide fragments thereof. By the administration of CRF-BP to treat such pregnancy-related disorders, these levels can be returned to normal and thus preserve the normal growth of the fetus, prevent early labor and achieve normal term delivery.

The present invention contemplates various immunoassay methods for determining the amount of CRF-BP in a biological fluid sample using a CRF-BP, a polypeptide fragment thereof, a polyclonal antibody or a monoclonal antibody of this invention as an immunochemical reagent to form an immunoreaction product whose amount relates, either directly or indirectly, to the amount of CRF-BP in the sample. Also contemplated are immunoassay methods for determining the amount of CRF peptide in a biological fluid sample using a CRF-BP or a polypeptide fragment thereof as a reagent to form a product whose amount relates, either directly or indirectly, to the amount of CRF in the sample. In addition, methods for determining the ratio of CRF to CRF-BP (CRF/CRF-BP) are also contemplated.

Various heterogenous and homogenous protocols, either competitive or noncompetitive, solution-phase or solid-phase, can be employed in performing an assay method of this invention. Those skilled in the art will understand that there are numerous, well known, clinical, diagnostic chemistry procedures in which an immunochemical reagent of this invention can be used to form an immunoreaction product whose amount relates to the amount of CRF-BP or CRF present in a body sample. Thus, while exemplary assay methods are described herein, the invention is not so limited.

The anti-CRF antibodies employed herein constitute a part of this invention only insofar as they are utilized with otherwise novel CRF-BP polypeptides, anti-CRF-BP antibodies, methods, and/or systems. Suitable anti-CRF antibodies, for example, are described in Menzaghi et al., *J. Neuroendocrinol.*, 3(5):469–475 (1991), Milton et al., *J. Mol. Endocrinol.*, 5(2):159–166 (1990), Van Oers et al., *Endocrinology*, 124(3):1239–1246 (1989). Alternatively, such can be produced against CRF, or a fragment thereof, as an immunogen using the methods described herein for producing anti-CRF-BP antibodies.

1. Noncompetitive Methods For Determining Levels of CRF-BP, CRF, and the CRF/CRF-BP ratio a. Determining the CRF-BP level For example, the present invention contemplates a solution-phase assay for the amount of CRF-BP in a single vascular fluid sample which comprises the steps of:
(a) forming an immunoreaction admixture by admixing a vascular fluid sample with:
 (1) anti-CRF-BP antibody molecules that immunoreact with:
  (i) isolated CRF-BP and
  (ii) CRF:CRF-BP complex; and
 (2) an anti-immunoglobulin antibody; and
(b) precipitating said immunoreaction admixture; and determining the amount of product that was formed.

Preferably, the vascular fluid sample is provided as a known amount of blood, or a blood-derived product such as serum or plasma. Regardless of the type of sample used, it is preferably obtained from a person who has fasted at least about 12 hours as is known in the art. Such a sample is referred to as a "fasting" sample. It is also noted that, where serum or plasma is used as the sample, the sample need not be subjected to treatment with a denaturing or chaotropic agent for purposes of altering the expression of the CRF-BP epitope being assayed.

Preferably, the amount of antibody that is admixed is known. Further preferred are embodiments where the anti-CRF-BP antibody, or the anti-immunoglobulin antibody that is directed against the anti-CRF-BP antibody, is labeled, i.e., operatively linked to an indicating means, such as an enzyme, a radionuclide or the like.

In a specific embodiment of the assay methods described herein, the anti-CRF-BP antibody is a polyclonal antibody prepared (e.g. as described in experimental Example 1 hereinafter) using a peptide in the form of amino acid residues 1-16 or 1-21 of the mature protein CRF-BP as the immunogen.

Precipitation of the immunoreaction complex containing the anti-immunoglobulin bound to the anti-CRF-BP, which is in turn bound to CRF-BP, is accomplished with polyethylene glycol (PEG).

b. Determining the CRF/CRF-BP ratio

An extension of the assay method described in section 1.a., above, is employed for determining the ratio of CRF/CRF-BP in a single vascular fluid sample. The additional steps include:

(c) forming two additional separate immunoreaction admixtures by admixing aliquots of said single vascular fluid sample from section 1.a. respectively with each of:

(1) an anti-CRF antibody containing antibody molecules that immunoreact with both isolated CRF and CRF:CRF-BP complex; and
an anti-immunoglobulin antibody; and (2) an anti-CRF antibody and an anti-CRF-BP antibody containing antibody molecules that immunoreact with CRF:CRF-BP complex, wherein either the anti-CRF or anti-CRF-BP antibody is labeled, and an anti-immunoglobulin antibody which is directed to the non-labeled one of the anti-CRF antibody and anti-CRF-BP antibody;

(d) precipitating each of said immunoreaction admixtures; and (e) determining the amount of product formed in each separate immunoreaction admixture of step (c).

In one embodiment, the anti-CRF-BP antibody is a rabbit anti-CRF-BP polyclonal antibody made against either hCRF-BP(1-16) or hCRF-BP(1-21). The anti-CRF antibody is a sheep anti-CRF antibody, preferably directed to residues 36-41 of r/hCRF (SEQ ID NO:7), and it is the labeled antibody of step (c)(2). The anti-immunoglobulin antibody is a sheep anti-rabbit-immunoglobulin directed to the rabbit anti-CRF-BP antibody.

In a preferred embodiment, the anti-CRF-BP antibody does not immunoreact with CRF-BP at a location that inhibits or disturbs the binding of CRF to CRF-BP, i.e. is substantially free of antibody molecules that so immunoreact. Likewise, the anti-CRF antibody does not immunoreact with CRF at a location that inhibits or disturbs the binding of CRF-BP to CRF, i.e. it is substantially free of antibody molecules that so immunoreact.

The amount of CRF-BP-containing, CRF-containing, and CRF:CRF-BP complex-containing immunoreaction products that form in each step is determined. Step (c)(1), above, measures the "total" CRF (i.e., the combined amount of "free" CRF and CRF:CRF-BP complex) in the sample; step (c)(2), above, measures the amount of CRF complexed (bound) to CRF-BP in the sample; and the assay method of section 1.a., above, measures the amount of "total" CRF-BP in the sample. From these results, the ratio of non-complexed CRF/CRF-BP is calculated.

In another embodiment of the assay methods described herein, when "total" CRF is being assayed, a CRF fragment or analog that does not immunoreact with the anti-CRF antibody employed in the assay can be added to the serum sample prior to the immunoreaction admixture formation step to effectively displace endogenous CRF bound to CRF-BP. For example, the r/hCRF fragment defined by amino acid residues 6-33 can be used to so displace CRF when anti-CRF(36-41) is employed. This should allow the "total" CRF present in the serum sample to be more accurately measured in its unbound form. It can be seen that r/hCRF(6-33) or analogs which bind to CRF-BP but do not exhibit significant CRF activity could therefore be used as a CRF-BP antagonist to complex with and tie-up the CRF-BP, displacing CRF.

Determining the amount of the CRF-BP-, CRF-, and CRF:CRF-BP complex-containing immunoreaction products, either directly or indirectly, can be accomplished by assay techniques well known in the art, the specifics of which typically depend on the type of indicating means used. In the assay methods described herein, the amount of product ultimately determined is related to the amount of immunoreaction product similarly formed and is determined using a control sample (in place of the vascular fluid sample) containing a known amount of a subject protein or polypeptide from which a standard curve is determined.

In the assay methods described herein, when the quantities of "total" CRF-BP, "total" CRF, and CRF:CRF-BP complex are known, the quantities of "free" CRF-BP (i.e., CRF-BP not bound to CRF) and "free" CRF can be calculated indirectly. For example, free CRF-BP is determined by subtracting the quantity of CRF:CRF-BP complex from total CRF-BP. Another example of calculating either "free" CRF or CRF-BP employs knowledge of the CRF:CRF-BP binding affinity constant ($k_a$) value, which equals 0.1 nM, in the formula:

$$k_a = [CRF:CRF-BP]/[CRF][CRF-BP],$$

wherein the amounts of CRF:CRF-BP complex and either free CRF or free CRF-BP have been determined as described herein.

c. Determining the CRF level

The present invention also contemplates a novel method for assaying the amount of free CRF (CRF that is not bound to CRF-BP) in a vascular fluid sample which comprises the steps of:

(a) forming an immunoreaction admixture by admixing a vascular fluid sample with:

(1) a CRF-BP protein or polypeptide fragment thereof which binds CRF, wherein the protein or CRF-BP fragment is operatively linked to a solid matrix such that the immunoreaction admixture has both a liquid phase and a solid phase; and (2) an anti-CRF antibody composition containing antibody molecules that immunoreact with isolated CRF and CRF:CRF-BP complex; and (b) maintaining said immunoreaction admixture for a time period sufficient to form a CRF:CRF-BP-containing immunoreaction product in the solid phase, and (c) determining the amount of product formed in step (b).

Briefly, CRF-BP, or a CRF-BP polypeptide fragment to which CRF binds, may be coated on a well in the solid phase. Next, the CRF-containing sample is added to such CRF-BP coated wells for a time sufficient to permit the free CRF peptide in the sample to bind to the solid phase CRF-BP. The serum sample is removed, and labeled anti-CRF antibodies that immunoreact with CRF:CRF-BP complex are added to determine the level of CRF bound to the coated CRF-BP in the solid phase, which is indicative of the level of free CRF in the sample.

2. Competitive Methods For Determining Levels of CRF-BP and the CRF/CRF-BP ratio a. Determining the CRF-BP level The present invention also contemplates a competitive method for assaying the amount of CRF-BP in a vascular fluid sample which comprises the steps of:
  (a) forming an immunoreaction admixture by admixing a vascular fluid sample with:
    (i) an anti-CRF-BP antibody of the present invention, and
    (ii) a CRF-BP or polypeptide fragment thereof of the present invention that is able to immunoreact with the added antibody.

In one embodiment, the diagnostic method includes:
  (a) forming an immunoreaction admixture by admixing a vascular fluid sample with:
    (1) an anti-CRF-BP antibody containing antibody molecules that immunoreact with isolated CRF-BP and CRF:CRF-BP complex; and
    (2) a CRF-BP protein or polypeptide fragment thereof, wherein one of either said protein or CRF-BP fragment, or said anti-CRF-BP antibody is operatively linked to a solid matrix such that the immunoreaction admixture has both a liquid phase and a solid phase;
  (b) maintaining said immunoreaction admixture for a time period sufficient to form a CRF-BP-containing immunoreaction product in the solid phase, and
  (c) determining the amount of product formed in step (b).

As previously indicated, the anti-CRF-BP antibody can be a monoclonal antibody prepared using, as an immunogen, an appropriate length sequence of the mature protein of SEQ ID NO:1 or NO:3.

Preferably, the CRF-BP or polypeptide fragment thereof is present as part of a solid support, i.e., operatively linked to a solid matrix, so that the immunoreaction admixture formed has a solid and a liquid phase. Further preferred are embodiments wherein the amount of protein or polypeptide present in the immunoreaction admixture is an amount sufficient to form an excess of epitopes relative to the number of antibody combining sites present in the immunoreaction admixture capable of immunoreacting with those epitopes.

(b) The immunoreaction admixture is maintained under biological assay conditions for a predetermined time period, e.g. about 10 minutes to about 16–20 hours, at a temperature of about 4° C. to about 45° C., such time being sufficient for the CRF-BP present in the sample to immunoreact with (immunologically bind) a portion of the anti-CRF-BP antibody combining sites present in the antibody to form a CRF-BP-containing immunoreaction product (immunocomplex). In embodiments where the protein or polypeptide is in the solid phase, the immunocomplex formed is also present in the solid phase.

Biological assay conditions are those that maintain the biological activity of the immunochemical reagents of this invention and the CRF-BP sought to be assayed. Those conditions include a temperature range of about 4° C. to about 45° C., a pH value range of about 5 to about 9, and an ionic strength varying from that of distilled water to that of about one molar sodium chloride. Methods for optimizing such conditions are well known in the art.

Exemplary of such a contemplated competitive diagnostic assay, wherein a CRF-BP protein or polypeptide fragment thereof is operatively linked to a solid matrix, is the ELISA assay described hereinafter.

b. Determining the CRF/CRF-BP ratio

An extension of the competitive assay method described in section 2.a., above, can also be employed for determining the ratio of CRF/CRF-BP in a vascular fluid sample where the additional steps include:
  (c) forming separate immunoreaction admixtures by admixing aliquots of said single vascular fluid sample from section 2.a. respectively with each of:
    (1) an anti-CRF antibody containing antibody molecules that immunoreact with isolated CRF and CRF:CRF-BP complex; and CRF or a fragment thereof,
      wherein one of either said CRF or CRF fragment, or said anti-CRF antibody is operatively linked to a solid matrix such that the immunoreaction admixture has both a liquid phase and a solid phase; and
    (2) an anti-CRF antibody and an anti-CRF-BP antibody containing antibody molecules that immunoreact with CRF:CRF-BP complex, wherein either the anti-CRF or anti-CRF-BP antibody is operatively linked to a solid matrix such that the immunoreaction admixture has both a liquid phase and a solid phase; and
  (d) maintaining said immunoreaction admixtures for a time period sufficient to form either a CRF, CRF-BP, or CRF/CRF-BP-containing immunoreaction product in the solid phase; and
  (e) determining the amount of product formed in each immunoreaction admixture in step (d).

From these results the desired ratio is calculated.

3. Sandwich ELISA Methods a. Determining the CRF-BP level

In another embodiment, the present invention contemplates a double antibody or "sandwich" immunoassay comprising the steps of:
  (a) forming a first immunoreaction admixture by admixing a vascular fluid sample with a first antibody, preferably a monoclonal antibody, wherein the antibody and CRF-BP and CRF:CRF-BP complex present in the sample are capable of forming a first immunoreaction product that can then immunoreact with a subject antibody, with the first antibody being preferably operatively linked to a solid matrix;
  (b) maintaining the first immunoreaction admixture so formed under biological assay conditions for a time period sufficient to form the first immunoreaction product and preferably then separating the first immunoreaction product from the sample;
  (c) forming a second immunoreaction admixture by admixing the first immunoreaction product with a second antibody, preferably a monoclonal antibody, wherein the second antibody and CRF-BP and CRF/CRF-BP complex present in the first immunoreaction product are capable of forming a second immunoreaction product;
  (d) maintaining the second immunoreaction admixture so formed under biological assay conditions for a time period sufficient to form a second or "sandwich" immunoreaction product; and
  (e) determining the amount of second immunoreaction product that is formed, and thereby the amount of CRF-BP in the sample.

Preferably, the subject antibody of step (c) is labeled, preferably with an enzyme; therefore, the second immunoreaction product formed is a labeled product.

When the antibodies of the above "sandwich" immunoassay are polyclonal, the first and second antibodies can be either the same or different. In one embodiment, the first and second antibodies are the same.

b. Determining the CRF/CRF-BP ratio

An extension of the assay method described in 3.a. through 3.e above can also be employed for determining the ratio of CRF/CRF-BP in a single vascular fluid sample comprising the steps of:

(f) forming separate immunoreaction admixtures by admixing aliquots of a single vascular fluid sample with each of:
  (1) two anti-CRF-BP antibodies containing antibody molecules that immunoreact with isolated CRF-BP and CRF:CRF-BP complex,
    wherein one of said anti-CRF-BP antibodies is operatively linked to a solid matrix such that the immunoreaction admixture has both a liquid phase and a solid phase, and wherein said two anti-CRF-BP antibodies are either the same or different; and
  (2) two anti-CRF antibodies containing antibody molecules that immunoreact with isolated CRF and CRF:CRF-BP complex,
    wherein one of said anti-CRF antibodies is operatively linked to a solid matrix such that the immunoreaction admixture has both a liquid phase and a solid phase, and wherein said two anti-CRF antibodies are either the same or different; and
  (3) an anti-CRF antibody and an anti-CRF-BP antibody containing antibody molecules that immunoreact with CRF:CRF-BP complex, wherein either the anti-CRF or anti-CRF-BP antibody is operatively linked to a solid matrix such that the immunoreaction admixture has both a liquid phase and a solid phase; and (g) maintaining the three immunoreaction admixtures for a time period sufficient to form either a CRF, CRF-BP, or CRF/CRF-BP-containing immunoreaction product in the solid phase; and (h) determining the amount of product formed in each immunoreaction admixture of step (g).

From these results the desired ratio is calculated.

In one embodiment, the detection of CRF-BP protein or polypeptide fragments in a body sample is utilized as a means to monitor the fate of therapeutically administered CRF-BP or polypeptide fragments according to the therapeutic methods disclosed herein.

Also contemplated are immunological assays capable of detecting the presence of immunoreaction product formation without the use of a label. Such methods employ a "detection means", which means are themselves well-known in clinical diagnostic chemistry and constitute a part of this invention only insofar as they are utilized with otherwise novel polypeptides, methods and systems. Exemplary detection means include methods known as biosensors and include biosensing methods based on detecting changes in the reflectivity of a surface, changes in the absorption of an evanescent wave by optical fibers or changes in the propagation of surface acoustical waves.

The nucleotide sequence encoding CRF-BP can itself be used in numerous assays as probes for genetic material present in naturally occurring materials. The analyte can be a nucleotide sequence which hybridizes with a probe comprising a sequence of at least about 14 or 17 consecutive nucleotides and usually 30 to 200 nucleotides; however, it can be any length sequence as long as the full sequence of SEQ ID NO:2. The analyte can be RNA or cDNA. In order to detect an analyte which hybridizes to a probe, the probe usually contains a detectable label as described elsewhere herewithin. One method for amplification of target nucleic acids, for later analysis by hybridization assays, is known as the polymerase chain reaction (PCR). PCR can be applied to detect CRF-BP in suspected samples using oligonucleotide primers spaced apart from each other and based on the subsequences of SEQ ID NO:2. The primers are complementary to opposite strands of a double-stranded DNA molecule and are typically separated by between about 50 to 450 nt or more (usually not more than 2000 nt). This method entails preparing the specific oligonucleotide primers and then carrying out repeated cycles of target DNA denaturation, primer binding, and extension with a DNA polymerase to obtain DNA fragments of the expected length based on the primer spacing.

The present invention contemplates therapeutic compositions useful for practicing the therapeutic methods described herein. Therapeutic compositions of the present invention contain a physiologically tolerable carrier together with a CRF-BP protein, CRF-BP polypeptide fragment, or anti-CRF-BP antibody, as described herein, dissolved or dispersed therein as an active ingredient. In a preferred embodiment, the therapeutic composition is not immunogenic when administered to a human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to a human without the production of undesirable physiological effects such as nausea, dizziness, gastric upset and the like.

The preparation of a pharmacological composition that contains active ingredients dissolved or dispersed therein is well understood in the art. Typically such compositions are prepared as injectables either as liquid solutions or suspensions; however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein which salts were hereinbefore described.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

As previously indicated, administration of the CRF-BPs or polypeptide fragments thereof is effective to reduce high ACTH levels in mammals caused by excessive CRF, which is referred to herein as "CRF-induced ACTH release." In this manner, the CRF-BPs are useful in treating high cortisol (i.e., glucocorticoids) levels which are associated with hypercortisolemia, Cushing's Disease, alcoholism, anorexia nervosa and similar diseases. Likewise, these CRF-BPs are considered to have utility in combatting pituitary tumors that produce CRF—particularly in maintaining stability in the patient until such a tumor can be surgically removed.

The CRF-BP proteins and fragments thereof are also useful to treat abnormalities which occur during the later stages of pregnancies; for example, they can be used to reduce pregnancy-induced complications and increased CRF levels which can otherwise result in excessive release of ACTH. In addition, CRF-BP proteins or fragments thereof can be administered to reduce the ratio of CRF/CRF-BP present in a patient. The IV administration of CRF-BPs may also be employed in certain instances to modulate blood pressure and thereby combat hypotension.

CRF has been reported to be elevated in the plasma of some patients with preeclampsia (toxemia of pregnancy). If this increased level of CRF is clinically significant, then the CRF-BP or an appropriate fragment thereof could be useful in the therapeutic management of preeclampsia. More particularly, CRF is a known modulator of the immune system, and it is considered that the administration of the protein CRF-BP may be useful to locally treat, i.e., by direct injection into the affected joint, arthritis and other similar ailments. It is also contemplated that CRF is elevated in the serum of AIDS patients; thus, CRF-BP or a fragment thereof could be administered to counteract immunosuppression of glucocorticoids. CRF is known to have a number of biological effects on the pituitary, and accordingly, the CRF-BP proteins can be used to modulate the action of CRF on the pituitary. Furthermore, it is well known that CRF has a number of biological effects in the brain; therefore, it is considered that the CRF-BP proteins can be effectively used to modulate the action of CRF on the brain, particularly with respect to control of appetite, reproduction, growth, anxiety, depression, fever and metabolism, as well as the regulation of blood pressure, heart rate and blood flow.

Thus, the present invention provides for a method for modulating the action of CRF in mammals comprising administering a therapeutically effective amount of a physiologically tolerable composition containing an CRF-BP protein or polypeptide fragment of the present invention.

In addition, the present invention provides a method for treating a pregnancy-related pathological disorder in mammals comprising administering a therapeutically effective amount of a physiologically tolerable composition containing a CRF-BP protein or polypeptide fragment of the present invention, said amount being effective to produce a CRF/CRF-BP ratio within the normal range for a pregnant female.

Also, as earlier indicated, the administration of anti-CRF-BP antibodies described herein is effective to modulate the biological effect of CRF-BPs when administered in vivo. For example, an anti-CRF-BP antibody of this invention can be used in the mammalian therapeutic methods, preferably human, to: neutralize or counteract the effect of CRF-BP, increase the level of free CRF (e.g., CRF not bound by CRF-BP), increase CRF-induced ACTH release, or increase the level of ACTH-induced glucocorticoids in a patient. Because increasing the level of free CRF increases the level of CRF-induced ACTH release, which increases glucocorticoid production, these therapeutic methods are useful for treating certain physiological conditions where increasing the level of glucocorticoids in a patient's vascular fluid is therapeutically effective, such as conditions of inflammation or Addison's Disease, and the like.

Administration of the antibodies for this purpose would be carried out along the lines and in amounts generally known in this art, and more particularly along the lines indicated herein with respect to administration of the protein itself.

A therapeutically effective amount is a predetermined amount calculated to achieve the desired effect, i.e., to decrease the amount of ACTH or decrease the CRF/CRF-BP ratio in a patient. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such compounds in depot or long-lasting form as discussed hereinafter. A therapeutically effective amount is typically an amount of a CRF-BP protein or polypeptide fragment thereof that, when administered in a physiologically tolerable composition, is sufficient to achieve a plasma concentration of from about 0.1 µg/ml to about 100 µg/ml, preferably from about 1.0 µg/ml to about 50 µg/ml, more preferably at least about 2 µg/ml and usually 5 to 10 µg/ml. Antibodies-are administered in proportionately appropriate amounts in accordance with known practices in this art.

The level of ACTH present in a patient, particularly in the plasma, can be readily determined by routine clinical analysis, and assays to monitor the level of ACTH are well known. In addition, changes in ACTH levels can be monitored during a treatment regimen to determine the effectiveness of the administered CRF-BP protein or polypeptide fragment over time.

Thus, the present therapeutic method provides a means for in vivo decreasing ACTH levels in a human patient displaying symptoms of elevated serum ACTH, or is otherwise at medical risk by the presence of serum ACTH, wherein it is beneficial to reduce the levels of ACTH by CRF-induced ACTH release. In addition, the present therapeutic method provides a means for in vivo decreasing ACTH-induced cortisol levels (e.g., glucocorticoids) in a human patient displaying symptoms of elevated serum cortisol.

Likewise, the CRF/CRF-BP ratio present in a patient, particularly in the plasma, can be readily determined by the diagnostic methods and kits provided herein and readily manipulated by administering CRF-BP, analogs thereof, or anti-CRF-BP antibodies. Exemplary assays to monitor the CRF/CRF-BP ratio are described hereinbefore. In addition, changes in CRF/CRF-BP ratio levels can be monitored during a treatment regimen to determine the effectiveness of the administered CRF-BP protein or polypeptide fragment over time.

Thus, the present therapeutic method provides a means for in vivo decreasing of the CRF/CRF-BP ratio in a human patient displaying symptoms of elevated serum CRF/CRF-BP levels, or is otherwise at medical risk by the presence of an elevated serum CRF/CRF-BP ratio, wherein it is beneficial to reduce the levels of free CRF (i.e., CRF not bound to CRF-BP) in the vascular fluid sample.

The CRF-BP protein or fragment thereof should be administered under the guidance of a physician, and pharmaceutical compositions will usually contain the protein in conjunction with a conventional, pharmaceutically-acceptable carrier. For treatment, substantially pure synthetic CRF-BP or a nontoxic salt thereof, combined with a pharmaceutically acceptable carrier to form a pharmaceutical composition, is preferably administered parenterally to mammals, including humans, either intravenously (IV), subcutaneously, intramuscularly, percutaneously, e.g. intranasally, or introcerebroventricularly; oral administration is possible with an appropriate carrier.

The therapeutic compositions containing a CRF-BP polypeptide of this invention are preferably administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

As an aid to the administration of effective amounts of a CRF-BP polypeptide, a diagnostic method of this invention for detecting a CRF-BP polypeptide in the subject's blood is useful to characterize the fate of the administered therapeutic composition.

It may also be desirable to deliver CRF-BP over prolonged periods of time, for example, for periods of one week to one year from a single administration, and slow release, depot or implant dosage forms may be utilized. For example, a dosage form may contain a pharmaceutically acceptable non-toxic salt of the compound which has a low degree of solubility in body fluids, for example, an acid addition salt with the polybasic acid; a salt with a polyvalent metal cation; or combination of the two salts. A relatively insoluble salt may also be formulated in a gel, for example, an aluminum stearate gel. A suitable slow release depot formulation for injection may also contain CRF-BP or a salt thereof dispersed or encapsulated in a slow degrading, non-toxic or non-antigenic polymer such as a polylactic acid/ polyglycolic acid polymer, for example, as described in U.S. Pat. No. 3,773,919. These compounds may also be formulated into silastic implants.

EXAMPLE 1

Preparation of Polyclonal Antisera to Synthetic Polypeptides

A. Preparation of Imnmunogen

An N-terminal CRF-BP fragment such as hCRF-BP(1-21) or hCRF-BP(1-16) is synthesized using the solid-phase technique described by Merrifield, *Adv. Enzymol.*, 32:221-96 (1969) as adapted for use with a Model 430A automated peptide synthesizer (Applied Biosystems, Foster, City, Calif.). The polypeptide-resin is cleaved by hydrogen fluoride, and the peptide is extracted and then analyzed for purity by high-performance liquid chromatography (HPLC) using a reverse-phase C18 column. (Waters Associates, Milford, Mass.). The polypeptide is coupled to a suitable carrier to form an immunogen.

B. Immunization and Collection of Polyclonal Antisera

The peptide-carrier immunogen is emulsified using the Ribi Adjuvant System (Ribi Immunochem Research, Inc., Hamilton, Montana) according to the manufacturer's instructions, and the peptide-carrier antigens are incorporated into the emulsion at a concentration of 300 µg/ml. Two rabbits are injected with 1 ml of a prepared emulsion after pre-immune serum samples are collected. The 1 ml emulsion dose is administered as follows: 0.30 ml intradermal (0.05 ml in each of 6 sites); 0.40 ml intramuscular (0.2 ml into each hind leg); 0.10 ml subcutaneous (neck region); and 0.20 ml intraperitoneal. The rabbits are injected 6 times at three-week intervals following the injection protocol as detailed. At one week after the second through sixth injections, blood samples are collected to check antibody titer against the specific peptide used as an immunogen by the SPRIA assay described below. The collected blood samples are stirred in a 37° C. oven for 1 hour, after which the samples are centrifuged at 3000×g for 20 minutes. The interface is collected and spun in a microfuge at 12,000×g for 5 minutes. The supernatant containing anti-peptide antibodies is collected and stored at −20° C.

The peptide antibody titers are determined by solid phase radioimmunoassay (SPRIA) essentially as described in Curtiss and Edgington, *J. Biol. Chem.*, 257:15213–15221 (1982). Briefly, 50 µl of PBS containing 5 µg/ml synthetic peptides are admixed into the wells of microtiter plates. The plates are maintained overnight (about 16 hours) at 4° C. to permit the peptides to adhere to well walls. After washing the wells four times with SPRIA buffer (2.68 mM KCL, 1.47 mM $KH_2PO_4$, 137 mM NaCl, 8.03 mM $Na_2HPO_4$, 0.05% Tween-20, 0.1 KIU/ml Traysol, 0.1% BSA, 0.015% $NAN_3$), 200 µl of SPRIA buffer containing 3% normal goat serum (NGS) and 3% bovine serum albumin (BSA) are admixed to each well to block excess protein binding sites. The plates are maintained for 30 minutes at 20° C., the wells emptied by shaking, and blotted dry to form a solid-support, i.e., a solid matrix to which the synthetic CRF-BP peptide immunogen is operatively affixed.

To each well is then admixed 50 µl of serum sample to form a solid-liquid phase immunoreaction admixture. The admixture is maintained for 2 hours at 37° C. to permit formation of solid-phase immunoreaction products. After washing the wells as previously described, 50 µl of $^{125}$I-labeled goat anti-rabbit IgG at 0.25 µg protein per ml are admixed to each well to form a labeling reaction admixture. That admixture is maintained for 1 hour at 37° C. to permit formation of $^{125}$I-labeled solid-phase immunoreaction products. After washing the wells as previously described, the amount of $^{125}$I-labeled product bound to each well is determined by gamma scintillation. Specific anti-peptide antibody titers in collected serum samples from immunized rabbits are determined in comparison to pre-immunized normal rabbit serum samples which are a measure of non-specific background. Serum samples are considered to contain anti-peptide polyclonal antibodies if the radioactive signal is 5 times over that seen with normal rabbit serum.

EXAMPLE 2

Preparation of Monoclonal Antibodies (Mabs)

A. Anti-peptide

A CRF-BP polypeptide is prepared as an immunogen according to Example 1. Balb/c ByJ mice (Scripps Research Institute Vivarium, La Jolla, Calif.) are immunized intraperitoneally (i.p.) with 50 µg of prepared peptide-carrier immunogens in complete Freund's adjuvant (CFA) followed by a second and third immunization using the same peptide-carrier immunogen, each about three weeks apart, in incomplete Freund's adjuvant (IFA). The mice receive a boost of 50 μg of prepared peptides intravenously in normal saline 4 days prior to fusion and a second similar perfusion boost one day later.

B. Preparation of Hybridomas

The animals so treated are sacrificed and the spleen of each mouse is harvested. A spleen cell suspension is then prepared. Spleen cells are then extracted from the spleen cell suspension by centrifugation for about 10 minutes at 1000 r.p.m., at 23° C. Following removal of supernatant, the cell pellet is resuspended in 5 ml cold $NH_4Cl$ lysing buffer, and is incubated for about 10 minutes.

To the lysed cell suspension are admixed 10 ml Dulbecco's Modified Eagle Medium (DMEM) (GIBCO) and HEPES [4-(2-hydroxyethyl)-1-piperidineethanesulfonic acid] buffer, and that admixture is centrifuged for about 10 minutes at 1000 r.p.m. at 23° C.

The supernatant is decanted, the pellet is resuspended in 15 ml of DMEM and HEPES, and is centrifuged for about 10 minutes at 1000 r.p.m. at 23° C. The above procedure is repeated.

The pellet is then resuspended in 5 ml DMEM and HEPES. An aliquot of the spleen cell suspension is then removed for counting. Fusions are accomplished in the following manner using the non-secreting mouse myeloma cell line P3X63Ag8.653.1, a subclone of line P3x63Ag 8.653 (ATCC 1580). Using a myeloma to spleen cell ratio of about 1 to 10 or about 1 to 5, a sufficient quantity of myeloma cells are centrifuged into a pellet, washed twice in 15 ml DMEM and HEPES, and centrifuged for about 10 minutes at 1000 r.p.m. at 23° C.

Spleen cells and myeloma cells are combined in round bottom 15 ml tubes. The cell mixture is centrifuged for 10 minutes at 100 r.p.m. at 23° C., and the supernatant is removed by aspiration. Thereafter, 200 μl of 50 percent (weight per volume) aqueous polyethylene glycol 4000 molecular weight (PEG; ATCC Baltimore, Md.) at about 37° C. are admixed using a 1 ml pipette with vigorous stirring to disrupt the pellet, and the cells are gently mixed for between 15 and 30 seconds. The cell mixture is centrifuged 4 minutes at 700 r.p.m.

At about 8 minutes from the time of adding the PEG, 5 ml of DMEM plus HEPES buffer are admixed slowly to the pellet, without disturbing the cells. After 1 minute, the resulting admixture is broken up with a 1 ml pipette, and is incubated for an additional 4 minutes. This mixture is centrifuged for 7 minutes at 1000 r.p.m. The supernatant is decanted, 5 ml of HT (hypoxanthine/thymidine) medium are slowly admixed to the pellet, and the admixture is maintained undisturbed for 5 minutes. The pellet is then broken into large chunks, and the final cell suspension is placed into T75 flasks (2.5 ml per flask) into which 7.5 ml HT medium have been placed previously. The resulting cell suspension is incubated at 37° C. to grow the fused cells. After 245 hours, 10 ml of HT medium are admixed to the flasks, followed 6 hours later by admixture of 0.3 ml of 0.04 mM aminopterin. 48 hours after fusion, 10 ml of HAT (hypoxanthine/aminopterin/thymidine) medium are admixed to the flasks.

Three days after fusion, viable cells are plated out in 96-well tissue culture plates at about $2 \times 10^4$ viable cells per well (768 total wells) in HAT buffer medium as described in Kennett et al., *Curr. Top. Microbiol. Immunol.*, 81:77 (1978). The cells are fed seven days after fusion with HAT medium and at approximately 4–5 day intervals thereafter as needed with HT medium. Growth is followed microscopically, and culture supernatants are collected about two weeks later and assayed for the presence of CRF-BP specific antibody by solid phase radioimmunoassay (RIA) essentially as described in Example 1.

Briefly, 50 μl of PBS containing 5 μg/ml of the prepared CRF-BP peptide immunogen or intact CRF-BP protein is admixed into the wells of microtiter plates. The plates are maintained overnight (about 16 hours) at 4° C. to permit the peptide or protein immunogen to adhere to well walls. After washing the wells four times with SPRIA buffer (2.68 mM KCl, 1.45 mM $KH_2PO_4$, 137 mM NaCl 8.03 mM $Na_2HPO_4$, 0.05% Tween-20, 0.1 KIU/ml Traysol, 0.1% BSA, 0.015% $NAN_3$), 200 μl of SPRIA buffer containing 3% normal goat serum (NGS) and 3% bovine serum albumin (BSA) are admixed to each well to block excess protein binding sites. The plates are maintained for 30 minutes at 20° C., the wells emptied by shaking, and blotted dry to form a solid-support, i.e., a solid matrix to which CRF-BP peptide immunogen or intact CRF-BP protein is operatively affixed.

To each well is then admixed 50 μl of hybridoma tissue culture supernatant to form a solid-liquid phase immunoreaction admixture. The admixture is maintained for 2 hours at 37° C. to permit formation of solid-phase immunoreaction products. After washing the wells as previously described, 50 μl of $^{125}$I-labeled goat anti-mouse IgG at 0.25 μg protein per ml are admixed to each well to form a labeling reaction admixture. That admixture is maintained for 1 hour at 37° C. to permit formation of $^{125}$I-labeled solid-phase immunoreaction products. After washing the wells as previously described, the amount of $^{125}$I-labeled product bound to each well is determined by gamma scintillation.

Hybridomas are selected from hybridoma cultures that secrete anti-CRF-BP antibodies into their culture media, and further characterized as described herein.

C. Monoclonal Antibody Preparation and Purification

Ascites fluids are obtained from separate sets of 10-week old Balb/c mice, which are first primed with 0.3 ml of mineral oil and then injected intraperitoneally with $5 \times 10^6$ of the hybridoma cells. The average time for development of ascites is 9 days. Following clarification by centrifugation at $15,000 \times g$ for 15 minutes at 23° C., ascites fluids produced by hybridomas are pooled and stored frozen at $-20°$ C.

Purified monoclonal antibodies (Mabs) from the hybridomas are prepared by fast protein liquid chromatography (FPLC) using a Pharmacia Mono Q HR5/5 anion exchange column (Pharmacia Fine Chemicals, Piscataway, N.J.) using a 0–0.5 molar (M) NaCl gradient in 10 mM Tris, pH 8.0 following directions supplied with the column. Purified Mabs are concentrated in an Amicon stirred ultrafiltration cell and stored as described hereinbefore.

EXAMPLE 3

Radio-labeling

Radioiodination of CRF-BP, a CRF-BP polypeptide, anti-CRF-BP antibodies and immunochemically purified goat anti-mouse Ig is performed utilizing the known Iodogen iodination procedure and Iodogen obtained from Pierce Biochemicals. Iodogen iodination is utilized to prepare the antigens and antibodies for use in solid phase radioimmunoassays as discussed below. Radio-labeling can also be performed employing chloramine T or Lacto peroxidase, or the like.

EXAMPLE 4

CRF-BP-Cyanogen Bromide Fragment Specificity

The CRF-BP fragment specificity of the antibodies prepared in Examples 1 and 2 is determined by Western blot analysis according to the method in Curtiss et al., Proceeding of the Workshop on Lipoprotein Heterogeneity, Ed. by Lippel, NIH Publication No. 87-2646 p. 363–377 (1987). Briefly, CNBr fragmentation is performed on isolated CRF-BP dissolved in 90% formic acid. CNBr is added in a 13,000 molar excess and the reaction mixture is maintained about 15 hours at about 20° C. Following lyophilization, the resulting CNBr fragments are solubilized in 1% SDS, 0.01M Tris, pH 8.2 and subjected to isoelectric focusing in 6% polyacrylamide slab gels containing 8M urea and 2% ampholine (pH 4 to pH 6) as described by Curtiss et al., *J. Biol. Chem.*, 260:2982–93 (1985). Electrophoretically separated proteins are transferred to nitrocellulose for separate immunoreaction with the antibodies. Production of immunoreaction products is detected by radioiodinated goat anti-mouse Ig followed by autoradiography.

The results of these studies indicate that the anti-CRF-BP peptide polyclonal and monoclonal antibodies immunoreact with only a subpopulation of the CNBr fragments produced, and not with all of the CNBr fragments. The CNBr immunoreactant results also indicate that the antibodies also immunoreact with isolated CRF-BP.

EXAMPLE 5

Solid-Phase Polypeptide ELISA

The CRF-BP polypeptides are tested for immunoreactivity with anti-CRF-BP antibodies in a direct binding ELISA. In the assay, 50 µg/ml of each polypeptide is dissolved in PBS to form a peptide coating solution, of which 150 µl is admixed into the wells of a flexible polyvinyl chloride microtiter plate (Immulon). The wells are then maintained about 16 to 20 hours at 4° C. to permit the peptide to absorb onto (coat) the walls of the wells. After removing the peptide coating solution by shaking, the wells are washed once with 350 µl of rinsing buffer (PBS containing 1 g/l BSA, 0.5 ml/l Tween-20, and 2 µl/l aprotinin). Excess protein binding sites are blocked by admixing 200 µl of blocking buffer (PBS containing 3% BSA) into each well, maintaining the wells for 1 hour at 37° C., removing the blocking buffer by shaking, and then washing the wells 3 times as previously described. The plate is then dried for 1 hour at 37° C. followed by addition of 100 µl of PBS containing 0.5 µg/ml horseradish peroxidase (HRPO) conjugated anti-CRF-BP peptide antibody to form a solid-liquid phase immunoreaction admixture. The resulting solid-liquid phase immunoreaction admixture is maintained at 20° C. for 1 hour to permit formation of a solid-phase polypeptide-containing immunoreaction product. The wells are then washed 3 times with rinsing buffer to remove unbound antibody.

The amount of immunoreaction product present in the solid phase is then determined by admixing two hundred microliters of OPD (O-phenylene diamine) substrate into each well to form a developing-reaction admixture. The admixture is maintained for 30 minutes at about 20° C. Subsequently, 50 µl of 4 N $H_2SO_4$ are admixed into each well to stop the developing-reaction, and the resulting solution is assayed for absorbance at 450 nanometers using a microtiter plate reader (Dynatech) to detect the amount of formed immunoreaction product.

To determine the relative effectiveness of anti-CRF-BP-peptide binding to CRF-BP synthetic polypeptides, a competition ELISA is performed with a synthetic CRF-BP polypeptide fragment as the test synthetic polypeptide in comparison to CRF-BP containing serum and purified CRF-BP. Microtiter plates are coated with the peptide fragment as described hereinbefore. After the drying step of the assay described hereinbefore, 50 µl of a fluid sample (i.e., a CRF-BP-containing fluid sample) or standard (i.e., a CRF-BP polypeptide) to be assayed are admixed into the polypeptide-coated well simultaneously with 50 µl of HRPO-conjugated anti-CRF-BP-peptide antibody to form an immunoreaction admixture. In the assay described herein, 3 competitors are tested for their ability to compete for binding of anti-CRF-BP-peptide antibody to the synthetic CRF-BP polypeptide antigen coated over a range of dilutions. First, the same polypeptide that was coated in the wells is added in liquid phase to separate coated wells at a starting concentration of 1 mg/ml and diluted 2-fold serially 6 times down to a final concentration of 0.0156 mg/ml. Second, serum samples derived from human plasma containing between 15–25 mg/ml of CRF-BP are added at a starting dilution of 1:10 and diluted 2-fold serially 6 times down to a final dilution of 1:320. Third, CRF-BP is added at a starting concentration of 1 mg/ml and diluted 2-fold 5 times down to a final concentration of 0.031 mg/ml. The plate is then incubated for 30 minutes at room temperature. The plate is washed and the assay developed as described hereinbefore to determine the amount of immunoreaction product formed, and thereby the amount of competitor present in the added fluid sample.

EXAMPLE 6

Antibody Immunoreactivity/Peptide Selection

The immunoreactivity of antibodies for native CRF-BP and their various respective synthetic polypeptides is examined by a competitive RIA performed as follows:

One hundred µl of PBS (0.15M NaCl, 0.01M $NaPo_4$, pH 7.2) containing 10 µg/ml CRF-BP are admixed to the wells of microtiter plates. The plates are maintained for 1 hour at 20° C. on a rotating platform to allow the CRF-BP to adhere to the wells and form solid supports. After aspirating excess liquid from the wells, 200 µl of block solution (3% BSA, 3% NGS in PBS) is admixed to each well, and the wells are maintained for 30 minutes at 20° C. on a rotating platform. Subsequently, the blocking solution is removed by aspiration, and the wells are washed 3 times with SPRIA buffer.

To each well is admixed, first, 50 µl of PBS containing 3% BSA and various concentrations of competitor antigen, i.e., CRF-BP peptide. Second, 50 µl of the anti-CRF-BP antibody (5 µg/ml for polyclonal antibody or clarified ascites diluted 1:11.25×$10^5$ for Mabs) in PBS containing 3% BSA is added to form competitive immunoreaction admixtures. In control wells, either competing antigen or antibody is replaced by PBS containing 3% BSA.

The immunoreaction admixtures are maintained about 15 hours at 4° C. on a rotating platform to permit formation of solid-phase immunoreaction products. After washing the wells as previously described, 100 µl of $^{125}$I-labeled goat anti-mouse-Ig directed to anti-CRF-BP Mabs, or $^{125}$I-labeled goat anti-rabbit Ig directed to anti-CRF-BP polyclonal antibodies, ($^{125}$I-goat anti-Ig diluted to 2×$10^5$ trichloracetic acid precipitable disintegrations per minute per 100 µl in PBS containing 3% BSA) are admixed to each well. The labeling immunoreaction admixtures so formed are maintained for 4 hours at 4° C. on a rotating platform. Subsequently, the wells are washed with SPRIA buffer as previously described, and the amount of $^{125}$I-labeled solid-phase immunoreaction product formed is determined in a gamma counter.

The ability of the anti-CRF-BP antibody to immunoreact with CRF-BP is compared by using CRF-BP and various synthetic peptides as competitors in the above-described RIA. The more efficiently a competitor binds to the primary antibody, the lower the $B/B_o$ values. $B/B_o$ represents corrected CPMs which are plotted against increasing concentrations of competition in μg/ml. $B/B_o$ values are determined in the following formula:

$$\frac{(\text{Competitor Sample } CPM - 0\% \ CPM)}{(100\% \ CPM - 0\% \ CPM)}$$

where 0% CPM is a measure of non-specific background based on CPM obtained in RIAs where wells coated with CRF-BP are reacted with the labeled secondary antibody in the absence of primary antibody and competitor, and where 100% CPM is a measure of the maximum non-competed binding of primary antibody to the substrate coated to the wells. Peptides with the lowest $B/B_o$ values are chosen as the preferred peptides for use in the diagnostic and therapeutic methods described herein.

Unless otherwise stated hereinbefore, all percentages are volume percents.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, biologically active fragments of such proteins, shortened at the C-terminus or at the N-terminus or at both termini, can be employed instead of the entire protein to have the same biological effect of modulating the bioactivity of CRF.

Particular features of the invention are emphasized in the claims which follow.

SEQUENCE LISTING SUMMARY

SEQ ID NO:1 is the amino acid sequence of the precursor of human CRF-BP.

SEQ ID NO:2 is the nucleic acid sequence from which SEQ ID NO:1 was deduced.

SEQ ID NO:3 is the amino acid sequence of the precursor of rat CRF-BP.

SEQ ID NO:4 is the nucleic acid sequence from which SEQ ID NO:3 was deduced.

SEQ ID NO:5 is an oligonucleotide used as a hybridization probe.

SEQ ID NO:6 is an oligonucleotide used as a hybridization probe.

SEQ ID NO:7 when the C-terminus is amidated is the amino acid sequence of r/hCRF.

What is claimed is:

1. An anti-corticotropin releasing factor binding protein (CRF-BP) antibody which immunoreacts with an epitope of mature human CRF-BP within the amino acid sequence: Tyr-Leu-Glu-Leu-Arg-Glu-Ala-Ala-Asp-Tyr-Asp-Pro-Phe-Leu-Leu-Phe and does not immunoreact with an epitope elsewhere in SEQ ID NO:1.

2. A diagnostic system, in kit form, comprising an amount of the anti-CRF-BP antibody of claim 1 sufficient to perform at least one assay.

3. The diagnostic system of claim 2 wherein said antibody is linked to a solid matrix.

4. The diagnostic system of claim 2 wherein said antibody is a monoclonal antibody.

5. An assay method for determining the amount of CRF-BP in a vascular fluid sample comprising the steps of:
  (a) forming an immunoreaction admixture by admixing a vascular fluid sample with a first anti-CRF-BP antibody according to claim 1 that immunoreacts with an epitope at the N-terminus of mature CRF-BP which is available to bind therewith in both isolated CRF-BP and CRF:CRF-BP complex; and
  (b) determining the amount of product formed in step (a).

6. A method for screening for pregnancy-induced hypertension or increased risk of premature labor in humans, which method comprises the steps of:
  (a) forming a first immunoreaction admixture by admixing an aliquot of a human vascular fluid sample with an anti-CRF-BP antibody according to claim 1 which immunoreacts with both isolated CRF-BP and CRF:CRF-BP complex;

(b) adding an anti-immunoglobulin antibody to said immunoreaction admixture of step (a); precipitating a product from said immunoreaction admixture of step (a) and determining the amount of said product formed therein;

(c) forming second and third separate immunoreaction admixtures by:

admixing a second aliquot of said vascular fluid sample with an anti-CRF antibody that specifically binds to an epitope within residues 36-41 rat/human corticotropin releasing factor (CRF) and therefore immunoreacts with both isolated CRF and CRF:CRF-BP complex, and with an anti-immunoglobulin antibody; and admixing a third aliquot of said vascular fluid sample with a mixture of (i) said anti-CRF antibody and (ii) said anti-CRF-BP antibody, wherein one of either (i) or (ii) is labeled with an indicating means and the other is not labeled, and with an anti-immunoglobulin antibody which is directed to said antibody that is not labeled;

(d) precipitating products from both of said second and third immunoreaction admixtures of step (c); and (e) determining the amount of product formed in each separate immunoreaction admixture of step (c) so as to provide the respective concentrations of CRF and CRF:CRF-BP;

(f) comparing the determined concentrations from steps (b) and (e) to calculate the ratio of CRF/CRF-BP; and (g) comparing said calculated CRF/CRF-BP ratio against ratios for normal pregnant females to detect an abnormally elevated CRF/CRF-BP ratio that is indicative of pregnancy-induced hypertension or increased risk of premature labor.

7. The method of screening according to claim 6 wherein an excess of CRF(6-33) is included in said second admixture, along with said anti-CRF antibody, to displace CRF from endogenous CRF:CRF-BP complex.

8. A method for screening for increased risk of premature labor in pregnancy by assaying a vascular fluid sample from a pregnant female, and comparing the CRF/CRF-BP ratio measured in such assay against ratios for normal pregnant females who do not have said pregnancy-related pathological disorders to detect an abnormally elevated CRF/CRF-BP ratio which is indicative of a potential disorder comprising:

(a) forming a first immunoreaction admixture by admixing a human vascular fluid sample with an anti-CRF-BP antibody according to claim 1 which immunoreacts with both CRF-BP and CRF:CRF-BP complex;

(b) adding an anti-immunoglobulin antibody to said immunoreaction admixture of step (a), thereby precipitating and then determining the amount of product formed in step (a); and (c) forming a second immunoreaction admixture by admixing another aliquot of said vascular fluid sample with (i) an anti-CRF antibody that immunoreacts with both isolated CRF and CRF:CRF-BP complex, wherein said anti-CRF antibody is directed to an epitope within residues 36-41 of CRF, and (ii) a CRF peptide fragment which is devoid of said epitope and which can displace CRF from endogenous complexes wherein one of either (i) said anti-CRF antibody, or (ii) said CRF fragment is linked to a solid matrix such that the immunoreaction admixture has both a liquid phase and a solid phase; and (d) determining the amount of immunoreaction product formed in the immunoreaction admixture of step (c); and (e) forming a third immunoreaction admixture by admixing another aliquot of said vascular sample with (A) an anti-CRF antibody which binds specifically to an epitope within residues 36-41 of CRF and (B) an anti-CRF-BP antibody which binds specifically to an epitope at the N-terminus of mature human CRF-BP which is found in residues 25-40 of SEQ ID NO:1, both of which antibodies immunoreact with CRF:CRF-BP complex, wherein only one of (A) or (B) is linked to a solid matrix such that the immunoreaction admixture has both a liquid phase and a solid phase, and wherein said (A) or (B) that is not operatively linked to said solid matrix is labeled with an indicating means;

(f) maintaining said third separate immunoreaction admixture for a time period sufficient to form an immunoreaction product in the solid phase, and determining the amount of immunoreaction product formed in the separate immunoreaction admixture of step (e); and comparing the amount of immunoreaction products from steps (a), (c), and (e) to determine the CRF/CRF-BP ratio in the vascular sample.

9. The assay method of claim 8 wherein said anti-CRF-BP antibody is created using Tyr-Leu-Glu-Leu-Arg-Glu-Ala-Ala-Asp-Tyr-Asp-Pro-Phe-Leu-Leu-Phe as an immunogen.

10. A method for screening for increased risk of a pregnancy-related pathological disorder, which method comprises carrying out the assay method of claim 9 using a vascular fluid sample from a pregnant female, and comparing the CRF/CRF-BP ratio measured against ratios for normal pregnant females to detect an abnormally elevated CRF/CRF-BP ratio that is indicative of pregnancy-induced hypertension or increased risk of premature labor.

11. An assay method for determining the ratio of CRF/CRF-BP in a vascular fluid sample comprising the steps of:

(a) forming a first immunoreaction admixture by admixing an aliquot of a vascular fluid sample with a first anti-CRF-BP antibody that immunoreacts with an epitope within residues 25-56 of SEQ ID NO:1 at the N-terminus of mature CRF-BP which is available to bind therewith both in isolated CRF-BP and in CRF:CRF-BP complex;

(b) adding an anti-immunoglobulin antibody to said immunoreaction admixture of step (a); precipitating said immunoreaction admixture of step (a) and determining the amount of product formed therein;

(c) forming separate second and third immunoreaction admixtures by:

admixing another aliquot of said vascular fluid sample with an anti-CRF antibody which binds specifically with an epitope within residues 36-41 of CRF and immunoreacts with both isolated CRF and CRF:CRF-BP complex, and with an anti-immunoglobulin antibody; and admixing still another aliquot of said vascular fluid sample with a mixture of (i) said anti-CRF antibody and (ii) an anti-CRF-BP antibody that immunoreacts with an epitope within residues 25-56 of SEQ ID NO:1 at the N-terminus of mature hCRF-BP, both (i) and (ii) immunoreacting with CRF:CRF-BP complex, wherein either (i) or (ii) is labeled with an indicating means and the other is not labeled, and with an anti-immunoglobulin antibody which specifically binds to said antibody that is not labeled;

(d) precipitating both of said separate immunoreaction admixtures of step (c); and (e) determining the amount of product formed in said second and third immunoreaction admixtures of step (c) so as to provide the respective concentrations of CRF and CRF:CRF-BP; and (f) comparing the determined concentrations from steps (b) and (e) to calculate the ratio of CRF/CRF-BP.

12. An assay method for determining the ratio of CRF/CRF-BP in a vascular fluid sample comprising the steps of:

(a) forming a first immunoreaction admixture by admixing a first aliquot of a vascular fluid sample with:

a first anti-CRF-BP antibody which specifically binds to an epitope within the sequence Tyr-Leu-Glu-Leu-Arg-Glu-Ala-Ala-Asp-Tyr-Asp-Pro-Phe-Leu-Leu-Phe-Ser-Ala-Asn-Leu-Lys and immunoreacts with both isolated hCRF-BP and CRF:CRF-BP complex, said first anti-CRF-BP antibody being linked to a solid matrix such that the immunoreaction admixture has both a liquid phase and a solid phase, and a second anti-CRF-BP antibody that immunoreacts with isolated hCRF-BP and CRF:CRF-BP complex, binding to a different epitope than said first anti-CRF-BP antibody, said second anti-CRF-BP antibody being labeled with an indicating means;

(b) forming separate second and third immunoreaction admixtures by:

admixing a second aliquot of said vascular fluid sample with first and second anti-CRF antibodies, one of said first and second anti-CRF antibodies specifically binding to an epitope within residues 36-41 of CRF and the other binding to a different epitope of CRF, wherein both of said first and second anti-CRF antibodies immunoreact with isolated CRF and CRF:CRF-BP complex, said first anti-CRF antibody being linked to a solid matrix such that the second immunoreaction admixture has both a liquid phase and a solid phase, and said second anti-CRF antibody being labeled with an indicating means; and admixing a third aliquot of said vascular fluid sample with a mixture of (A) an anti-CRF antibody directed to an epitope within residues 36-41 of CRF and (B) an anti-CRF-BP antibody directed to an epitope within the sequence Tyr-Leu-Glu-Leu-Arg-Glu-Ala-Ala-Asp-Tyr-Asp-Pro-Phe-Leu-Leu-Phe-Ser-Ala-Asn-Leu-Lys, both said antibodies immunoreacting with CRF:CRF-BP complex, wherein only one of (A) or (B) is linked to a solid matrix such that the third immunoreaction admixture has both a liquid phase and a solid phase, and wherein the other of (A) or (B) is labeled with an indicating means;

(c) maintaining said three separate immunoreaction admixtures for time periods sufficient to form immunoreaction products in the solid phase; and (d) determining the amount of immunoreaction product formed in each separate immunoreaction admixture of steps (a) and (b), to determine CRF-BP, CRF and CRF:CRF-BP, respectively; and (e) comparing the determined concentrations from step (d) to calculate the ratio of CRF/CRF-BP.

13. The assay method of claim 12 for determining the ratio of CRF/CRF-BP wherein an excess of CRF(6-33) is added to said second admixture, along with the said first and second anti-CRF antibody, to displace CRF from the endogenous CRF:CRF-BP complex.

14. The assay method of claim 12 wherein said first anti-CRF-BP antibody is created using Tyr-Leu-Glu-Leu-Arg-Glu-Ala-Ala-Asp-Tyr-Asp-Pro-Phe-Leu-Leu-Phe as an immunogen.

15. A method for screening for a pregnancy-related pathological disorder, which method comprises carrying out the assay method of claim 12 using a vascular fluid sample from a pregnant female, and comparing the CRF/CRF-BP ratio measured against ratios for normal pregnant females to detect an abnormally elevated CRF/CRF-BP ratio that is indicative of pregnancy-induced hypertension or increased risk of premature labor.

16. A method of assaying the amount of free CRF in a vascular fluid sample of a human comprising the steps of:

(a) forming an admixture by admixing a vascular fluid sample with:

a substantially pure recombinant hCRF-BP protein having amino acid SEQ ID NO:1 or a polypeptide fragment thereof which is shortened by elimination of a sequence beginning at the C-terminus and/or the N-terminus, which fragment binds to human CRF and when bound prevents human CRF from complexing with its receptor, said protein or polypeptide fragment thereof being linked to a solid matrix such that the admixture has both a liquid phase and a solid phase;

(b) maintaining said admixture for a time period sufficient for free CRF in said sample to form a CRF:CRF-BP-containing complex, then removing said serum sample and admixing an anti-CRF antibody which specifically binds to an epitope within residues 36-41 of CRF and immunoreacts with CRF:CRF-BP complex to form a CRF:CRF-BP-containing immunoreaction product in the solid phase; and (c) determining the amount of immunoreaction product formed in step (b) which is indicative of the level of free CRF in said sample.

17. An assay method for determining the ratio of CRF/CRF-BP in a vascular fluid sample comprising the steps of:

(a) forming a first immunoreaction admixture by admixing an aliquot of a vascular fluid sample with an anti-CRF-BP antibody that immunoreacts with mature CRF-BP both in free form and in CRF:CRF-BP complex, a known amount of CRF-BP or a fragment thereof which immunoreacts with said anti-CRF-BP antibody wherein one of either (i) said CRF-BP or fragment thereof or (ii) said anti-CRF-BP antibody is linked to a solid matrix such that said first immunoreaction admixture has both a liquid phase and a solid phase;

(b) maintaining said first immunoreaction admixture for a time period sufficient to form a CRF-BP-containing immunoreaction product in the solid phase and determining the total amount of CRF-BP in said aliquot;

(c) forming separate second and third immunoreaction admixtures by:

admixing another aliquot of said vascular fluid sample with an anti-CRF antibody which binds specifically with an epitope within residues 36-41 of CRF and immunoreacts with both free CRF and CRF:CRF-BP complex, and with a known amount of CRF wherein one of either said CRF or said anti-CRF antibody is linked to a solid matrix such that said second immunoreaction admixture has both a liquid phase and a solid phase; and admixing still another aliquot of said vascular fluid sample with a mixture of (i) said anti-CRF antibody and (ii) an anti-CRF-BP antibody that immunoreacts with an epitope within residues 25-56 of SEQ ID NO:1 at the N-terminus of mature CRF-BP, both (i) and (ii) immunoreacting with CRF:CRF-BP complex, wherein either (i) or (ii) is labeled with an indicating means and the other is linked to a solid matrix;

(d) maintaining both of said separate immunoreaction admixtures of step (c) for a time period sufficient to form an immunoreaction product in the solid phase; and (e) determining the amount of product formed in said second and third immunoreaction admixtures of step (c) so as to provide the respective concentrations of free CRF and of CRF:CRF-BP; and (f) comparing the determined concentrations from steps (b) and (e) to calculate the ratio of free CRF to free CRF-BP.

18. The assay method of claim 17 wherein in step (c), CRF(6-33) is added to said another aliquot in said second immunoreaction admixture.

* * * * *

UNITED STATES PATENT AND TRADEMARK OFFICE
CERTIFICATE OF CORRECTION

PATENT NO : 5,733,790
DATED : March 31, 1998
INVENTOR(S): Potter, et al.

It is certified that error appears in the above-identified patent and that said Letters Patent is hereby corrected as shown below:

Title Page [63], last line, change "Nov. 15, 1991" to --Jan. 15, 1991--.

Signed and Sealed this

Ninth Day of June, 1998

*Attest:*

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 322 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Met  Ser  Pro  Asn  Phe  Lys  Leu  Gln  Cys  His  Phe  Ile  Leu  Ile  Phe  Leu
1                   5                        10                       15

Thr  Ala  Leu  Arg  Gly  Glu  Ser  Arg  Tyr  Leu  Glu  Leu  Arg  Glu  Ala  Ala
               20                       25                       30

Asp  Tyr  Asp  Pro  Phe  Leu  Leu  Phe  Ser  Ala  Asn  Leu  Lys  Arg  Glu  Leu
          35                       40                       45

Ala  Gly  Glu  Gln  Pro  Tyr  Arg  Arg  Ala  Leu  Arg  Cys  Leu  Asp  Met  Leu
     50                       55                       60

Ser  Leu  Gln  Gly  Gln  Phe  Thr  Phe  Thr  Ala  Asp  Arg  Pro  Gln  Leu  His
65                            70                       75                  80

Cys  Ala  Ala  Phe  Phe  Ile  Ser  Glu  Pro  Glu  Glu  Phe  Ile  Thr  Ile  His
                    85                       90                       95

Tyr  Asp  Gln  Val  Ser  Ile  Asp  Cys  Gln  Gly  Gly  Asp  Phe  Leu  Lys  Val
               100                      105                      110

Phe  Asp  Gly  Trp  Ile  Leu  Lys  Gly  Glu  Lys  Phe  Pro  Ser  Ser  Gln  Asp
          115                      120                      125

His  Pro  Leu  Pro  Ser  Ala  Glu  Arg  Tyr  Ile  Asp  Phe  Cys  Glu  Ser  Gly
     130                      135                      140
```

| | | | | | | | | | | | | | | | |
|---|---|---|---|---|---|---|---|---|---|---|---|---|---|---|---|
| Leu | Ser | Arg | Arg | Ser | Ile | Arg | Ser | Ser | Gln | Asn | Val | Ala | Met | Ile | Phe |
| 145 | | | | | 150 | | | | | 155 | | | | | 160 |
| Phe | Arg | Val | His | Glu | Pro | Gly | Asn | Gly | Phe | Thr | Leu | Thr | Ile | Lys | Thr |
| | | | | 165 | | | | | 170 | | | | | 175 | |
| Asp | Pro | Asn | Leu | Phe | Pro | Cys | Asn | Val | Ile | Ser | Gln | Thr | Pro | Asn | Gly |
| | | | 180 | | | | | 185 | | | | | 190 | | |
| Lys | Phe | Thr | Leu | Val | Val | Pro | His | Gln | His | Arg | Asn | Cys | Ser | Phe | Ser |
| | | 195 | | | | | 200 | | | | | 205 | | | |
| Ile | Ile | Tyr | Pro | Val | Val | Ile | Lys | Ile | Ser | Asp | Leu | Thr | Leu | Gly | His |
| | 210 | | | | | 215 | | | | | 220 | | | | |
| Val | Asn | Gly | Leu | Gln | Leu | Lys | Lys | Ser | Ser | Ala | Gly | Cys | Glu | Gly | Ile |
| 225 | | | | | 230 | | | | | 235 | | | | | 240 |
| Gly | Asp | Phe | Val | Glu | Leu | Leu | Gly | Gly | Thr | Gly | Leu | Asp | Pro | Ser | Lys |
| | | | | 245 | | | | | 250 | | | | | 255 | |
| Met | Thr | Pro | Leu | Ala | Asp | Leu | Cys | Tyr | Pro | Phe | His | Gly | Pro | Ala | Gln |
| | | | 260 | | | | | 265 | | | | | 270 | | |
| Met | Lys | Val | Gly | Cys | Asp | Asn | Thr | Val | Val | Arg | Met | Val | Ser | Ser | Gly |
| | | 275 | | | | | 280 | | | | | 285 | | | |
| Lys | His | Val | Asn | Arg | Val | Thr | Phe | Glu | Tyr | Arg | Gln | Leu | Glu | Pro | Tyr |
| | 290 | | | | | 295 | | | | | 300 | | | | |
| Glu | Leu | Glu | Asn | Pro | Asn | Gly | Asn | Ser | Ile | Gly | Glu | Phe | Cys | Leu | Ser |
| 305 | | | | | 310 | | | | | 315 | | | | | 320 |
| Gly | Leu | | | | | | | | | | | | | | |

( 2 ) INFORMATION FOR SEQ ID NO:2:

( i ) SEQUENCE CHARACTERISTICS:
        ( A ) LENGTH: 1246 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 45..1013

( i x ) FEATURE:
        ( A ) NAME/KEY: mat_peptide
        ( B ) LOCATION: 117..320

( x i ) SEQUENCE DESCRIPTION: SEQ ID NO:2:

| | | | | | | | | | | | | |
|---|---|---|---|---|---|---|---|---|---|---|---|---|
| GGACCTCCGG | AGCAGAGCAC | AGCAGCTGCA | GAGGCAAGGC | CAGC | ATG | TCG | CCC | AAC | | | | 56 |
| | | | | | Met | Ser | Pro | Asn | | | | |
| | | | | | -24 | | | | | | | |

| | | | | | | | | | | | | | | | |
|---|---|---|---|---|---|---|---|---|---|---|---|---|---|---|---|
| TTC | AAA | CTT | CAG | TGT | CAC | TTC | ATT | CTC | ATC | TTC | CTG | ACG | GCT | CTA | AGA | 104 |
| Phe | Lys | Leu | Gln | Cys | His | Phe | Ile | Leu | Ile | Phe | Leu | Thr | Ala | Leu | Arg |
| -20 | | | | | -15 | | | | | -10 | | | | | -5 |

| | | | | | | | | | | | | | | |
|---|---|---|---|---|---|---|---|---|---|---|---|---|---|---|
| GGG | GAA | AGC | CGG | TAC | CTA | GAG | CTG | AGG | GAA | GCG | GCG | GAC | TAC | GAT | CCT | 152 |
| Gly | Glu | Ser | Arg | Tyr | Leu | Glu | Leu | Arg | Glu | Ala | Ala | Asp | Tyr | Asp | Pro |
| | | | | 1 | | | | | 5 | | | | | 10 | |

| | | | | | | | | | | | | | | | |
|---|---|---|---|---|---|---|---|---|---|---|---|---|---|---|---|
| TTC | CTG | CTC | TTC | AGC | GCC | AAC | CTG | AAG | CGG | GAG | CTG | GCT | GGG | GAG | CAG | 200 |
| Phe | Leu | Leu | Phe | Ser | Ala | Asn | Leu | Lys | Arg | Glu | Leu | Ala | Gly | Glu | Gln |
| | | | | 15 | | | | | 20 | | | | | 25 | |

| | | | | | | | | | | | | | | | |
|---|---|---|---|---|---|---|---|---|---|---|---|---|---|---|---|
| CCG | TAC | CGC | CGC | GCT | CTG | CGG | TGC | CTG | GAC | ATG | CTG | AGC | CTC | CAG | GGC | 248 |
| Pro | Tyr | Arg | Arg | Ala | Leu | Arg | Cys | Leu | Asp | Met | Leu | Ser | Leu | Gln | Gly |
| | | 30 | | | | | 35 | | | | | 40 | | | |

| | | | | | | | | | | | | | | | |
|---|---|---|---|---|---|---|---|---|---|---|---|---|---|---|---|
| CAG | TTC | ACC | TTC | ACC | GCC | GAC | CGG | CCG | CAG | CTG | CAC | TGC | GCA | GCC | TTC | 296 |
| Gln | Phe | Thr | Phe | Thr | Ala | Asp | Arg | Pro | Gln | Leu | His | Cys | Ala | Ala | Phe |
| 45 | | | | | 50 | | | | | 55 | | | | | 60 |

| | | | | | | | | | | | | | | | | |
|---|---|---|---|---|---|---|---|---|---|---|---|---|---|---|---|---|
|TTC|ATC|AGC|GAG|CCC|GAG|GAG|TTC|ATT|ACC|ATC|CAC|TAC|GAC|CAG|GTC|344|
|Phe|Ile|Ser|Glu|Pro|Glu|Glu|Phe|Ile|Thr|Ile|His|Tyr|Asp|Gln|Val| |
| | | | |65| | | | |70| | | | |75| | |

```
TTC ATC AGC GAG CCC GAG GAG TTC ATT ACC ATC CAC TAC GAC CAG GTC         344
Phe Ile Ser Glu Pro Glu Glu Phe Ile Thr Ile His Tyr Asp Gln Val
             65              70                      75

TCC ATC GAC TGT CAG GGC GGC GAC TTC CTG AAG GTA TTT GAT GGT TGG         392
Ser Ile Asp Cys Gln Gly Gly Asp Phe Leu Lys Val Phe Asp Gly Trp
             80              85                      90

ATT CTC AAG GGG GAG AAG TTC CCC AGT TCC CAG GAT CAT CCT CTC CCC         440
Ile Leu Lys Gly Glu Lys Phe Pro Ser Ser Gln Asp His Pro Leu Pro
         95             100                     105

TCA GCT GAG CGG TAC ATA GAT TTC TGT GAG AGT GGT CTT AGC AGG AGG         488
Ser Ala Glu Arg Tyr Ile Asp Phe Cys Glu Ser Gly Leu Ser Arg Arg
        110             115                     120

AGC ATC AGA TCT TCC CAG AAT GTG GCC ATG ATC TTC TTC CGA GTC CAT         536
Ser Ile Arg Ser Ser Gln Asn Val Ala Met Ile Phe Phe Arg Val His
125             130                     135                     140

GAA CCA GGA AAT GGA TTC ACA TTA ACC ATA AAG ACA GAC CCC AAC CTC         584
Glu Pro Gly Asn Gly Phe Thr Leu Thr Ile Lys Thr Asp Pro Asn Leu
                145                     150                     155

TTT CCT TGC AAT GTC ATT TCT CAG ACT CCA AAT GGA AAG TTT ACC CTG         632
Phe Pro Cys Asn Val Ile Ser Gln Thr Pro Asn Gly Lys Phe Thr Leu
            160                     165                     170

GTA GTT CCA CAC CAG CAT CGA AAC TGC AGC TTC TCC ATA ATT TAT CCT         680
Val Val Pro His Gln His Arg Asn Cys Ser Phe Ser Ile Ile Tyr Pro
            175                     180                     185

GTG GTG ATC AAA ATA TCT GAT CTT ACC CTG GGA CAC GTA AAT GGT CTT         728
Val Val Ile Lys Ile Ser Asp Leu Thr Leu Gly His Val Asn Gly Leu
            190                     195                     200

CAG TTA AAG AAA TCC TCA GCA GGT TGC GAG GGA ATA GGA GAC TTT GTG         776
Gln Leu Lys Lys Ser Ser Ala Gly Cys Glu Gly Ile Gly Asp Phe Val
205                     210                     215                 220

GAG CTG CTG GGA GGA ACT GGA TTG GAC CCT TCC AAG ATG ACG CCT TTA         824
Glu Leu Leu Gly Gly Thr Gly Leu Asp Pro Ser Lys Met Thr Pro Leu
                    225                     230                     235

GCT GAT CTC TGC TAC CCC TTT CAT GGC CCG GCC CAG ATG AAA GTT GGC         872
Ala Asp Leu Cys Tyr Pro Phe His Gly Pro Ala Gln Met Lys Val Gly
            240                     245                     250

TGT GAC AAC ACT GTG GTG CGC ATG GTC TCC AGT GGA AAA CAC GTA AAT         920
Cys Asp Asn Thr Val Val Arg Met Val Ser Ser Gly Lys His Val Asn
            255                     260                     265

CGT GTG ACT TTT GAG TAT CGT CAG CTG GAG CCG TAC GAG CTG GAA AAC         968
Arg Val Thr Phe Glu Tyr Arg Gln Leu Glu Pro Tyr Glu Leu Glu Asn
270                     275                     280

CCA AAT GGA AAC AGT ATC GGG GAA TTC TGT TTG TCT GGT CTT TGA            1013
Pro Asn Gly Asn Ser Ile Gly Glu Phe Cys Leu Ser Gly Leu *
285                     290                     295

ATAACCAACC CAGTGATTTA CATGCTGATA GCTAAGTGAG TTTTAATGG CCATTGTGTA       1073

TGATTTTGAT GCACAACTAG TTAAAAGCCT TTCATACCAG TCAGTATTTC CCAGCCTTGA      1133

GCGCACGCAC ACACCACACA CATACACACA CGCATTATTT TTGTTACTTT GCTTCTTTTT      1193

ATGTTTGTAA TCTGTAAATG AACACATGGC AGAAAATAAC CCTGATTGGT AGG            1246
```

( 2 ) INFORMATION FOR SEQ ID NO:3:

( i ) SEQUENCE CHARACTERISTICS:
        ( A ) LENGTH: 322 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| Met | Ser | Pro | Asn | Phe | Lys | Leu | Gln | Cys | His | Phe | Thr | Leu | Ile | Leu | Leu |
|---|---|---|---|---|---|---|---|---|---|---|---|---|---|---|---|
| 1 | | | | 5 | | | | | 10 | | | | | 15 | |
| Thr | Ala | Leu | Arg | Gly | Glu | Ser | Arg | Tyr | Leu | Glu | Val | Gln | Glu | Ala | Ala |
| | | | 20 | | | | | 25 | | | | | 30 | | |
| Val | Tyr | Asp | Pro | Phe | Leu | Leu | Phe | Ser | Ala | Asn | Leu | Lys | Arg | Asn | Leu |
| | | | 35 | | | | 40 | | | | | 45 | | | |
| Ala | Glu | Glu | Gln | Pro | Tyr | Arg | Arg | Ala | Leu | Arg | Cys | Leu | Asp | Met | Leu |
| | 50 | | | | | 55 | | | | | 60 | | | | |
| Ser | Leu | Pro | Gly | Gln | Phe | Thr | Phe | Thr | Ala | Asp | Gln | Pro | Gln | Leu | His |
| 65 | | | | | 70 | | | | | 75 | | | | | 80 |
| Cys | Ala | Ala | Phe | Phe | Ile | Gly | Glu | Pro | Glu | Glu | Phe | Ile | Thr | Ile | His |
| | | | | 85 | | | | | 90 | | | | | 95 | |
| Phe | Asp | Leu | Val | Ser | Ile | Asp | Cys | Gln | Gly | Gly | Asp | Phe | Leu | Lys | Val |
| | | | 100 | | | | | 105 | | | | | 110 | | |
| Phe | Asp | Gly | Trp | Ile | Leu | Lys | Gly | Glu | Lys | Phe | Pro | Ser | Ser | Gln | Asp |
| | | 115 | | | | | 120 | | | | | 125 | | | |
| His | Pro | Leu | Pro | Thr | Arg | Glu | Arg | Tyr | Thr | Asp | Phe | Cys | Glu | Ser | Gly |
| | 130 | | | | | 135 | | | | | 140 | | | | |
| Leu | Thr | Arg | Arg | Ser | Val | Thr | Ser | Ser | Gln | Asn | Val | Ala | Met | Val | Phe |
| 145 | | | | | 150 | | | | | 155 | | | | | 160 |
| Phe | Arg | Val | His | Glu | Pro | Gly | Asn | Gly | Phe | Thr | Ile | Thr | Ile | Lys | Thr |
| | | | | 165 | | | | | 170 | | | | | 175 | |
| Asp | Pro | Asn | Leu | Phe | Pro | Cys | Asn | Ile | Ile | Ser | Gln | Thr | Pro | Ser | Gly |
| | | | 180 | | | | | 185 | | | | | 190 | | |
| Arg | Phe | Ala | Leu | Val | Val | Pro | Tyr | Gln | His | Gln | Asn | Cys | Ser | Phe | Ser |
| | | 195 | | | | | 200 | | | | | 205 | | | |
| Ile | Ile | Tyr | Pro | Val | Thr | Ile | Lys | Ile | Ser | Asp | Leu | Ala | Leu | Gly | His |
| | 210 | | | | | 215 | | | | | 220 | | | | |
| Leu | His | Gly | Leu | Gln | Leu | Lys | Lys | Pro | Ala | Ala | Gly | Cys | Gly | Gly | Thr |
| 225 | | | | | 230 | | | | | 235 | | | | | 240 |
| Gly | Asp | Phe | Val | Glu | Leu | Leu | Gly | Gly | Thr | Gly | Leu | Asp | Thr | Ser | Lys |
| | | | | 245 | | | | | 250 | | | | | 255 | |
| Met | Met | Leu | Leu | Val | Asp | Leu | Cys | Tyr | Pro | Phe | His | Gly | Pro | Ala | Gln |
| | | | 260 | | | | | 265 | | | | | 270 | | |
| Met | Lys | Ile | Ser | Cys | Asp | Asn | Ala | Val | Val | Arg | Met | Val | Ser | Ser | Gly |
| | | 275 | | | | | 280 | | | | | 285 | | | |
| Lys | His | Met | Asn | Arg | Val | Thr | Phe | Glu | Tyr | Arg | Gln | Leu | Glu | Pro | Leu |
| | 290 | | | | | 295 | | | | | 300 | | | | |
| Glu | Leu | Glu | Thr | Ser | Thr | Arg | Asn | Ser | Ile | Pro | Glu | Tyr | Cys | Leu | Ser |
| 305 | | | | | 310 | | | | | 315 | | | | | 320 |
| Ser | Leu | | | | | | | | | | | | | | |

( 2 ) INFORMATION FOR SEQ ID NO:4:

( i ) SEQUENCE CHARACTERISTICS:
        ( A ) LENGTH: 1095 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 118..1086

( i x ) FEATURE:
        ( A ) NAME/KEY: mat_peptide
        ( B ) LOCATION: 190..1086

(xi) SEQUENCE DESCRIPTION: SEQ ID NO:4:

```
AAAGAGACCC AGGAAAGGAC CCTAGCAGCT TCGAGTTCTC AGTGTGGGCG AAGGCGAGGG         60

AAGAAACGCC TAAGATCTCC GCAGCCGAGC TCACCAGCTG CAGACACAAG GCCAGCC          117

ATG TCA CCG AAC TTC AAA CTC CAA TGC CAC TTC ACT CTG ATC CTC CTG         165
Met Ser Pro Asn Phe Lys Leu Gln Cys His Phe Thr Leu Ile Leu Leu
-24             -20                 -15                 -10

ACA GCT CTA AGG GGA GAG AGC CGC TAC CTA GAG GTG CAA GAA GCC GCA         213
Thr Ala Leu Arg Gly Glu Ser Arg Tyr Leu Glu Val Gln Glu Ala Ala
             -5                  1                   5

GTC TAC GAC CCT TTC CTG CTT TTC AGC GCC AAT TTG AAG CGG AAC CTG         261
Val Tyr Asp Pro Phe Leu Leu Phe Ser Ala Asn Leu Lys Arg Asn Leu
         10                  15                  20

GCA GAG GAG CAG CCC TAC CGA CGG GCT CTG CGC TGC CTG GAC ATG CTG         309
Ala Glu Glu Gln Pro Tyr Arg Arg Ala Leu Arg Cys Leu Asp Met Leu
 25                  30                  35                  40

AGC CTC CCT GGC CAG TTC ACC TTC ACC GCT GAC CAG CCG CAG CTG CAC         357
Ser Leu Pro Gly Gln Phe Thr Phe Thr Ala Asp Gln Pro Gln Leu His
                     45                  50                  55

TGC GCC GCC TTC TTC ATC GGC GAG CCG GAG GAG TTC ATC ACC ATC CAC         405
Cys Ala Ala Phe Phe Ile Gly Glu Pro Glu Glu Phe Ile Thr Ile His
                 60                  65                  70

TTT GAC CTG GTC TCC ATC GAC TGC CAG GGT GGG GAT TTC CTG AAG GTA         453
Phe Asp Leu Val Ser Ile Asp Cys Gln Gly Gly Asp Phe Leu Lys Val
             75                  80                  85

TTT GAT GGT TGG ATC CTT AAG GGG GAG AAG TTC CCA AGT TCT CAG GAT         501
Phe Asp Gly Trp Ile Leu Lys Gly Glu Lys Phe Pro Ser Ser Gln Asp
         90                  95                  100

CAC CCT CTG CCC ACC AGG GAG AGG TAC ACA GAT TTC TGT GAG AGC GGT         549
His Pro Leu Pro Thr Arg Glu Arg Tyr Thr Asp Phe Cys Glu Ser Gly
105                  110                 115                 120

CTC ACC AGA AGG AGT GTT ACA TCT TCC CAG AAT GTG GCC ATG GTC TTC         597
Leu Thr Arg Arg Ser Val Thr Ser Ser Gln Asn Val Ala Met Val Phe
                 125                 130                 135

TTC CGG GTC CAT GAA CCA GGA AAT GGA TTC ACG ATA ACC ATA AAG ACA         645
Phe Arg Val His Glu Pro Gly Asn Gly Phe Thr Ile Thr Ile Lys Thr
             140                 145                 150

GAC CCC AAC CTC TTC CCT TGC AAT ATC ATC TCT CAG ACT CCG AGT GGA         693
Asp Pro Asn Leu Phe Pro Cys Asn Ile Ile Ser Gln Thr Pro Ser Gly
         155                 160                 165

AGA TTT GCT TTG GTG GTT CCA TAC CAG CAC CAA AAC TGC AGC TTT TCC         741
Arg Phe Ala Leu Val Val Pro Tyr Gln His Gln Asn Cys Ser Phe Ser
     170                 175                 180

ATC ATT TAT CCG GTG ACC ATC AAA ATC TCT GAC CTC GCC CTG GGA CAC         789
Ile Ile Tyr Pro Val Thr Ile Lys Ile Ser Asp Leu Ala Leu Gly His
185                 190                 195                 200

CTG CAT GGC CTT CAG TTG AAG AAA CCT GCG GCT GGC TGT GGT GGA ACT         837
Leu His Gly Leu Gln Leu Lys Lys Pro Ala Ala Gly Cys Gly Gly Thr
                 205                 210                 215

GGA GAC TTT GTG GAG CTG CTG GGA GGA ACT GGA CTG GAC ACC TCC AAG         885
Gly Asp Phe Val Glu Leu Leu Gly Gly Thr Gly Leu Asp Thr Ser Lys
             220                 225                 230

ATG ATG CTC TTA GTG GAC CTG TGT TAC CCC TTT CAT GGC CCT GCC CAG         933
Met Met Leu Leu Val Asp Leu Cys Tyr Pro Phe His Gly Pro Ala Gln
         235                 240                 245

ATG AAA ATT AGC TGC GAC AAT GCT GTG GTG AGG ATG GTC TCC AGT GGA         981
Met Lys Ile Ser Cys Asp Asn Ala Val Val Arg Met Val Ser Ser Gly
250                 255                 260

AAA CAC ATG AAC CGT GTG ACT TTT GAG TAT CGT CAG CTG GAA CCA CTC        1029
```

| | | | | | | | | | | | | | | | | |
|---|---|---|---|---|---|---|---|---|---|---|---|---|---|---|---|---|
| Lys | His | Met | Asn | Arg | Val | Thr | Phe | Glu | Tyr | Arg | Gln | Leu | Glu | Pro | Leu | |
| 265 | | | | | 270 | | | | | 275 | | | | | 280 | |
| GAG | CTG | GAA | ACC | TCG | ACC | AGA | AAC | AGC | ATC | CCG | GAG | TAC | TGC | TTG | TCT | 1077 |
| Glu | Leu | Glu | Thr | Ser | Thr | Arg | Asn | Ser | Ile | Pro | Glu | Tyr | Cys | Leu | Ser | |
| | | | | 285 | | | | | 290 | | | | | 295 | | |
| AGT | CTT | TGA | ATGACCAGC | | | | | | | | | | | | | 1095 |
| Ser | Leu | * | | | | | | | | | | | | | | |

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide"

( x i ) SEQUENCE DESCRIPTION: SEQ ID NO:5:

GAYTAYGATC CNTTYYTNYT NTTYWS-     33
NGCN AAC ( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide"

( x i ) SEQUENCE DESCRIPTION: SEQ ID NO:6:

CARAAYGTNT GCNATGATNT TYTTC     25

( 2 ) INFORMATION FOR SEQ ID NO:7:

( i ) SEQUENCE CHARACTERISTICS:
        ( A ) LENGTH: 41 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

| | | | | | | | | | | | | | | |
|---|---|---|---|---|---|---|---|---|---|---|---|---|---|---|
| Ser | Glu | Glu | Pro | Pro | Ile | Ser | Leu | Asp | Leu | Thr | Phe | His | Leu | Leu | Arg |
| 1 | | | | 5 | | | | | 10 | | | | | 15 | |
| Glu | Val | Leu | Glu | Met | Ala | Arg | Ala | Glu | Gln | Leu | Ala | Gln | Gln | Ala | His |
| | | | 20 | | | | | 25 | | | | | 30 | | |
| Ser | Asn | Arg | Lys | Leu | Met | Glu | Ile | Ile | | | | | | | |
| | | | 35 | | | | | 40 | | | | | | | |